(12) United States Patent
Chuang et al.

(10) Patent No.: US 12,380,555 B2
(45) Date of Patent: Aug. 5, 2025

(54) CONVOLUTIONAL NEURAL NETWORKS FOR CLASSIFICATION OF CANCER HISTOLOGICAL IMAGES

(71) Applicants: The Jackson Laboratory, Bar Harbor, ME (US); Jeffrey Hsu-Min Chuang, West Hartford, CT (US); Javad Noorbakhsh, Cambridge, MA (US); Ali Foroughi pour, Bristol, CT (US); Kourosh Zarringhalam, Arlington, MA (US); Saman Farahmand, Quincy, MA (US); Mohammad Soltanieh-ha, Cambridge, MA (US)

(72) Inventors: Jeffrey Hsu-Min Chuang, West Hartford, CT (US); Javad Noorbakhsh, Cambridge, MA (US); Ali Foroughi pour, Bristol, CT (US); Kourosh Zarringhalam, Arlington, MA (US); Saman Farahmand, Quincy, MA (US); Mohammad Soltanieh-ha, Cambridge, MA (US)

(73) Assignee: The Jackson Laboratory, Bar Harbor, ME (US)

( * ) Notice: Subject to any disclaimer, the term of this patent is extended or adjusted under 35 U.S.C. 154(b) by 602 days.

(21) Appl. No.: 17/628,144

(22) PCT Filed: Jul. 17, 2020

(86) PCT No.: PCT/US2020/042675
§ 371 (c)(1),
(2) Date: Jan. 18, 2022

(87) PCT Pub. No.: WO2021/016131
PCT Pub. Date: Jan. 28, 2021

(65) Prior Publication Data
US 2022/0270244 A1  Aug. 25, 2022

Related U.S. Application Data

(60) Provisional application No. 62/876,563, filed on Jul. 19, 2019.

(51) Int. Cl.
*G06T 7/00* (2017.01)
*G01N 33/483* (2006.01)
(Continued)

(52) U.S. Cl.
CPC ....... *G06T 7/0012* (2013.01); *G01N 33/4833* (2013.01); *G06N 3/063* (2013.01);
(Continued)

(58) Field of Classification Search
CPC .................. G06T 7/0012; G06T 7/194; G06T 2207/20081; G06T 2207/20084;
(Continued)

(56) References Cited

U.S. PATENT DOCUMENTS

2018/0312908 A1   11/2018   Ruan et al.

FOREIGN PATENT DOCUMENTS

| EP | 3705025 A1 * | 9/2020 | ......... A61B 1/00009 |
| WO | WO-2015177268 A1 * | 11/2015 | ......... G06K 9/00127 |

(Continued)

OTHER PUBLICATIONS

Noorbakhsh Javad et al: "Pan-cancer Classifications of tumor histological images using deep learning", bioRxiv, Jul. 26, 2019 (Jul. 26, 2019), XP093069340, DOI: 10.1101/715656, URL:https://www.biorxiv.org/content/10.1101/715656v1.full.pdf. (Year: 2019).*

(Continued)

*Primary Examiner* — John J Lee
(74) *Attorney, Agent, or Firm* — Wolf, Greenfield & Sacks, P.C.

(57) ABSTRACT

Techniques for classifying, using a deep learning model, histopathological whole slide images (WSIs) as comprising
(Continued)

images of cancerous or non-cancerous tissue and/or as comprising images of cancerous tissue having a genetic mutation or not having a genetic mutation are described herein. The techniques include at least one processor configured to instantiate a container-based processing architecture to train and/or use the deep learning model to process and classify at least one WSI. In some embodiments, a treatment may be selected and administered based on a classification result obtained from the deep learning model.

15 Claims, 25 Drawing Sheets

(51) Int. Cl.
*G06N 3/063* (2023.01)
*G06N 3/08* (2023.01)
*G06T 7/194* (2017.01)

(52) U.S. Cl.
CPC ............... *G06N 3/08* (2013.01); *G06T 7/194* (2017.01); *G06T 2207/20081* (2013.01); *G06T 2207/20084* (2013.01); *G06T 2207/30024* (2013.01)

(58) Field of Classification Search
CPC ...... G06T 2207/30024; G01N 33/4833; G06N 3/063; G06N 3/08
See application file for complete search history.

(56) References Cited

FOREIGN PATENT DOCUMENTS

| WO | WO 2018/049250 A1 | 3/2018 | |
|---|---|---|---|
| WO | WO 2019/084697 A1 | 5/2019 | |
| WO | WO-2019105976 A1 * | 6/2019 | ......... G01N 15/1475 |

OTHER PUBLICATIONS

Coudray Nicolas et al: "Classification and mutation prediction from non-small cell lung cancer histopathology images using deep learning", vol. 24, No. 10, Sep. 17, 2018 (Sep. 17, 2018), pp. 1559-1567, XP036608997, ISSN: 1078-8956. (Year: 2018).*
International Search Report and Written Opinion for International Application No. PCT/US2020/042675, mailed Oct. 15, 2020.
International Preliminary Report on Patentability for International Application No. PCT/US2020/042675, mailed Feb. 3, 2022.
PCT/US2020/042675, Oct. 15, 2020, International Search Report and Written Opinion.
PCT/US2020/042675, Feb. 3, 2022, International Preliminary Report on Patentability.
Extended European Search Report for European Application No. 20843864.8, dated Aug. 22, 2023.
Coudray et al., Classification and mutation prediction from non-small cell lung cancer histopathology images using deep learning. Nature Medicine. Oct. 2018;24(10):1559-67.
Noorbakhsh et al., Pan-cancer classifications of tumor histological images using deep learning. BioRxiv preprint. https://www.biorxiv.org/content/10.1101/715656v1. Jul. 2019:1-24.
Schaumberg et al., H&E-stained whole slide image deep learning predicts SPOP mutation state in prostate cancer. BioRxiv preprint. https://www.biorxiv.org/content/10.1101/064279v9.full. Jul. 17, 2016:1-11.
Yim et al., Image analysis of HER2 immunohistochemical staining of surgical breast cancer specimens. Yonsei Medical Journal. Feb. 1, 2019;60(2):158-62.

* cited by examiner

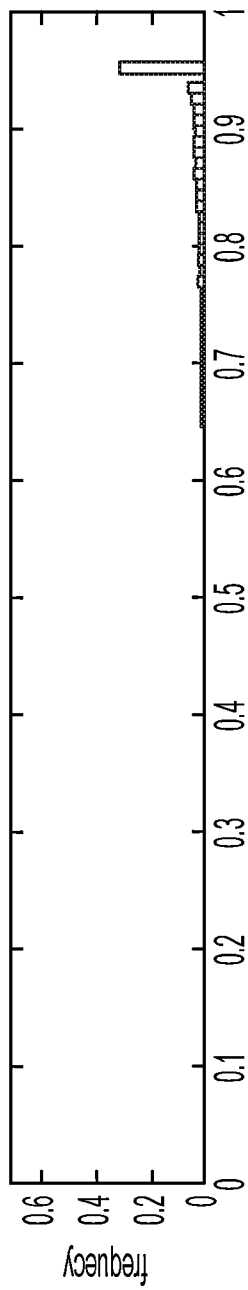
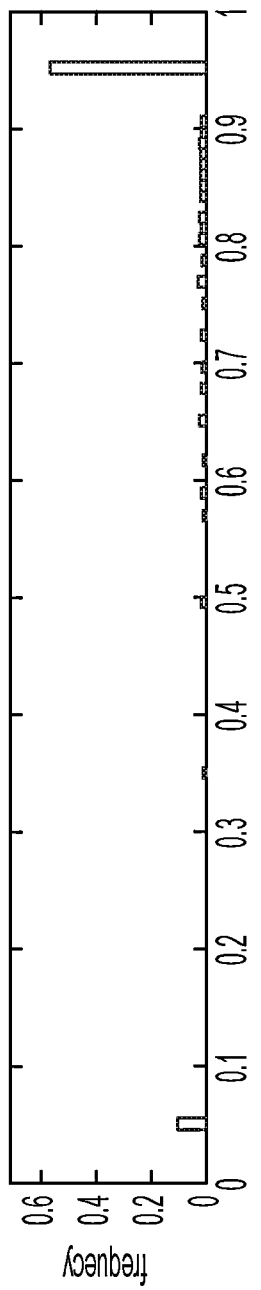
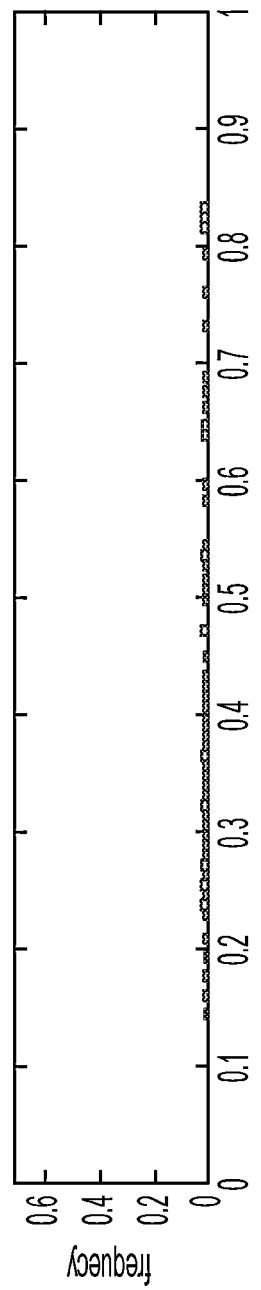
FIG. 16A  Tumor purity of breast cancer 512-by-512 tiles
FIG. 16B  Tumor purity of breast cancer 256-by-256 tiles
FIG. 16C  Tumor purity of colon cancer 512-by-512 tiles

CONVOLUTIONAL NEURAL NETWORKS FOR CLASSIFICATION OF CANCER HISTOLOGICAL IMAGES

CROSS-REFERENCE TO RELATED APPLICATIONS

This Application is a national stage filing under 35 U.S.C. § 371 of International Patent Application Serial No. PCT/US2020/042675, filed Jul. 17, 2020, which claims the benefit under 35 U.S.C. § 119(e) of U.S. Provisional Application Ser. No. 62/876,563, filed Jul. 19, 2019. The contents of these applications are incorporated herein by reference in their entireties.

GOVERNMENT FUNDING

This invention was made with government support under R01CA230031 awarded by the National Cancer Institute at the National Institutes of Health. The government has certain rights in the invention.

BACKGROUND

Visual analysis of histopathological images is used to make cancer diagnoses and selecting appropriate treatment methods. Conventional analysis of histopathological images involves manual inspection of images of tissue samples by trained pathologists, which may be time consuming and prone to intra- and inter-observer variability.

SUMMARY

Provided herein, in some aspects, is a system and method for classifying histopathological images of tissue samples as comprising images of cancerous or non-cancerous tissue, as comprising images of cancerous tissue comprising a genetic mutation or no genetic mutation, and selecting and administering treatment to a patient based on the classification results.

Some embodiments are directed to a system for identifying cancerous tissue in a tissue sample, the system comprising: at least one processor operatively connected to a memory containing instructions which, when executed by the at least one processor, cause the at least one processor to: instantiate a container-based processing architecture comprising: a first container configured to process at least one whole slide image (WSI) of the tissue sample to obtain an at least one processed WSI; a second container configured to provide the at least one processed WSI as input to a trained deep learning model to obtain feature values output by the trained deep learning model; and a third container configured to classify the at least one WSI as one of an image comprising non-cancerous tissue or an image comprising cancerous tissue based on the feature values.

Some embodiments are directed to at least one non-transitory computer readable storage medium storing processor-executable instructions that, when executed by at least one processor, cause the at least one processor to perform a method comprising: processing at least one whole slide image (WSI) of a tissue sample; and classifying, using a trained deep learning model, the at least one WSI as comprising one of an image comprising cancerous tissue or an image comprising non-cancerous tissue, wherein: at least one layer of the trained deep learning model is trained based on a first training data set comprising WSIs of a plurality of tissue types, and at least one layer of the trained deep learning model is trained based on a second training data set comprising non-histological images.

Some embodiments are directed to a method for identifying cancerous tissue in a whole slide image (WSI) of a tissue sample, the method comprising: processing at least one WSI of the tissue sample; and classifying, using a trained deep learning model, the at least one WSI as comprising one of an image comprising cancerous tissue or an image comprising non-cancerous tissue, wherein: at least one layer of the trained deep learning model is trained based on a first training data set comprising WSIs of a plurality of tissue types, and at least one layer of the trained deep learning model is trained based on a second training data set comprising non-histological images.

Some embodiments are directed to a method for identifying a genetic mutation of a cancerous tissue sample based on a whole slide image (WSI) of the cancerous tissue sample, the method comprising: processing at least one WSI of the cancerous tissue sample; and classifying, using a trained deep learning model, the at least one WSI as an image comprising one of cancerous tissue having a genetic mutation or one of cancerous tissue lacking a genetic mutation.

Some embodiments are directed to at least one non-transitory computer readable storage medium storing processor-executable instructions that, when executed by at least one processor, cause the at least one processor to perform a method comprising: processing at least one WSI of a cancerous tissue sample; and classifying, using a trained deep learning model, the at least one WSI as comprising one of an image of cancerous tissue having a genetic mutation or one of an image comprising cancerous tissue lacking a genetic mutation.

Some embodiments are directed to a system for identifying a genetic mutation of a cancerous tissue sample, the system comprising: at least one processor operatively connected to a memory containing instructions which, when executed by the at least one processor, cause the at least one processor to: instantiate a container-based processing architecture comprising: a first container configured to process at least one whole slide image (WSI) of the cancerous tissue sample to obtain an at least one processed WSI; a second container configured to provide the at least one processed WSI as input to a trained deep learning model to obtain feature values output by the trained deep learning model; and a third container configured to classify the at least one WSI as one of an image of cancerous tissue having a genetic mutation or one of an image comprising cancerous tissue lacking a genetic mutation based on the feature values.

It should be appreciated that all combinations of the foregoing concepts and additional concepts discussed in greater detail below (provided such concepts are not mutually inconsistent) are contemplated s being a part of the inventive subject matter disclosed herein.

BRIEF DESCRIPTION OF DRAWINGS

Various aspects and embodiments will be described with reference to the following figures. It should be appreciated that the figures are not necessarily drawn to scale. In the drawings, each identical or nearly identical component that is illustrated in various figures is represented by a like numeral. For purposes of clarity, not every component may be labeled in every drawing.

FIG. 16 shows a histogram of tumor purity for breast and colon cancer regions of interest.

DETAILED DESCRIPTION

Figure 1A:
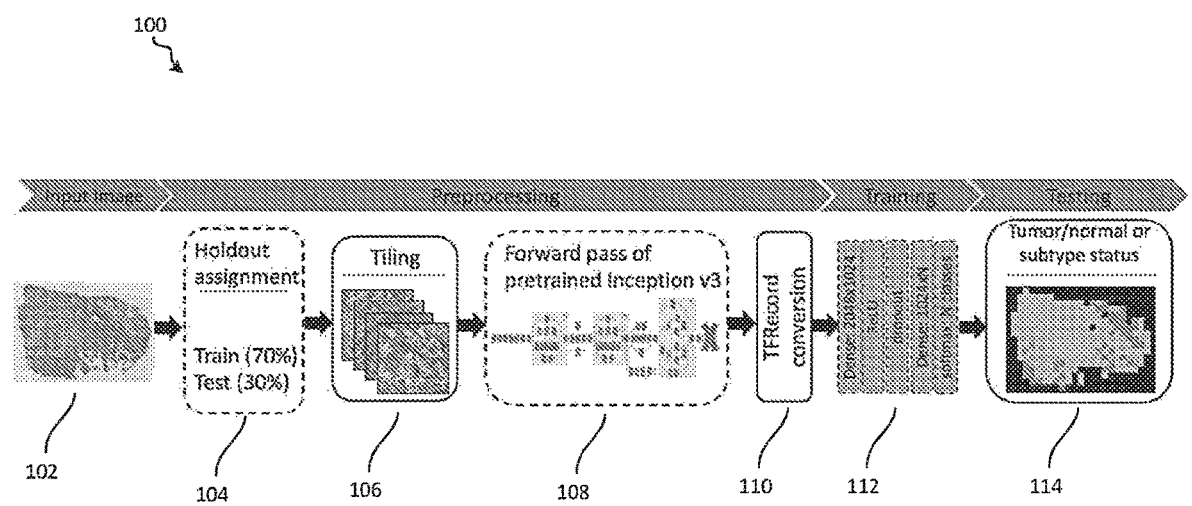
FIG. 1A depicts, schematically, a system for performing classification of histopathological images using a container-based processing architecture and a deep learning model, according to some embodiments.

Analysis of histopathological images may be used to diagnose cancer subtypes and tumor stage as well as in selecting an optimal treatment modality. Conventional analysis of such histopathological images (e.g., whole slide images (WSIs)) requires manual classification of imaged tissues by trained pathologists. Such manual analysis involves assessments of image features by trained pathologists and may be time consuming and costly. In the case of borderline diagnoses, manual analysis may also be prone to intra- and inter-pathologist variability. Additionally, histopathological images are a rich but incompletely explored data type for the bioinformatic study of cancer. However, because manual inspection is time consuming, histopathological images are a challenging source of data for image data mining. The inventors have recognized that advances in computational image analysis and classification provide opportunities for the application of computation image analysis to such histopathological images.

In the last few years, there have been major advances in supervised and unsupervised learning in computational image analysis and classification (Russakovsky et al. 2015; Litjens et al. 2017), providing opportunities for application to tumor histopathology. Manual analysis involves assessments of features such as cellular morphology, nuclear structure, or tissue architecture, and such pre-specified image features have been inputted into support vector machines or random forests for tumor subtype classification and survival outcome analysis, e.g. (Luo et al. 2017; Yu et al. 2016; Mousavi et al. 2015). However, these pre-specified features may not generalize well across tumor types, so recent studies have focused on approaches using convolutional neural networks (CNNs), bypassing the feature specification step. For example, Schaumberg et. al., trained ResNet-50 CNNs to predict SPOP mutations using WSIs from 177 prostate cancer patients (Schaumberg, Rubin, and Fuchs 2018), achieving AUC=0.74 in cross-validation and AUC=0.64 on an independent cohort. Yu et al., utilized CNN architectures including AlexNet, GoogLeNet, VGGNet-16 (Simonyan and Zisserman 2014), and ResNet-50 to identify transcriptomic subtypes of lung adenocarcinoma (LUAD) and squamous cell carcinoma (LUSC) (Yu et al. 2019). They were able to classify LUAD vs. LUSC (AUC of 0.88-0.93), as well as each vs. adjacent benign tissues with higher accuracy. Moreover, they were able to predict the TCGA transcriptomic classical, basal, secretory, and primitive subtypes of LUAD (Wilkerson et al. 2010, 2012) with AUCs 0.77-0.89, and similar subtype classifications have been reported for breast cancer tissue (Couture et al. 2019). Recently, Coudray et al. (Coudray et al. 2018) proposed a CNN based on Inception v3 architecture to classify WSIs in LUAD and LUSC, achieving an AUC of 0.99 in classification of cancerous and non-cancerous tissues. Further, their models were able to predict mutations in 10 genes in LUAD with AUCs 0.64-0.86, and subsequently mutations in BRAF (AUC~0.75) or NRAS (AUC~0.77) melanomas (Kim et al. 2019). Other groups have used CNNs to distinguish tumors with high or low mutation burden (Xu et al. 2019). These advances highlight the potential of CNNs in computer assisted analysis of WSIs.

These prior studies have focused on individual cancer types, but little investigation has been done on how neural networks trained on one cancer type perform on other cancer types. Accordingly, the inventors developed systems and methods for the application and use of deep learning models across cancer types, enabling accurate WSI classification and comparisons that reveal shared spatial behaviors of cancerous tissues. Deep learning models are a class of machine learning algorithms that use multiple, connected layers to progressively simplify and/or transform input data as the data is passed through each layer. The inventors have recognized and appreciated that a trained deep learning model utilizing convolutional neural networks (CNNs) may be able to overcome the aforementioned challenges associated with manual classification and analysis of WSIs, making cancer diagnosis and treatment faster and more accurate.

The inventors have further recognized and appreciated that a challenge for the use of deep learning models in analyzing WSIs for cancer diagnoses has been the selection and construction of the training set of images. For example, prior studies have focused on individual cancer types, but there has been little investigation of how neural networks trained on one cancer type perform on other cancer types, which could provide important biological insights. As an analogy, comparisons of sequences from different cancers have revealed common driver mutations, e.g. both breast and gastric cancers have frequent HER2 genetic mutations, and both are susceptible to treatment by trastuzumab. Such analysis is in a rudimentary state for image data, as it remains unclear how commonly spatial behaviors are shared between cancer types.

Conventionally, it has been assumed that the training set must contain WSIs of the tissue type that is to be classified (e.g., a deep learning model for kidney cancer detection should be trained using WSIs of only kidney tissues and tumors). The inventors have recognized and appreciated that training a deep learning model using WSIs from more than one type of tissues (e.g., a combination of gastrointestinal, gynecological, kidney, breast, etc.) and/or cancer subtypes may increase versatility of the deep learning model. Using WSIs representing a variety of tissues in the training set of images may reduce the need for developing specialized image pre-processing for each variety of tissue and/or cancer subtype. The inventors have accordingly developed image processing and convolutional neural network software that can be broadly applied across tumor types to enable cross-tissue analyses by analyzing 27,815 frozen or formalin-fixed, paraffin-embedded (FFPE) whole-slide hematoxylin and eosin stain (H&E) images from 23 cohorts from The Cancer Genome Atlas (TCGA), a resource with centralized rules for image collection, sequencing, and sample processing. Using these techniques, the inventors have developed a CNN architecture can distinguish whether a WSI indicated cancerous or non-cancerous tissue and/or can classify particular cancer subtypes in a wide range of tissue types.

Accordingly, systems and methods for a "pan-cancer" approach to training a deep learning model for WSI classification are presented herein. The inventors have, by systematically comparing the ability of neural networks trained on one cancer type to classify images from another cancer type, recognized that deep learning models recapitulate known tissue biology in cross-classification relationships. For example, these comparisons reveal that breast, bladder, and uterine cancers can be considered canonical cancer image types for the classification of WSIs.

The inventors have further recognized and appreciated that the use of transfer learning may positively impact the field of cancer image analysis. Transfer learning is used to pre-train neural networks using existing image compilations, after which the pre-trained neural networks may be applied to related but different image classification problems. However, standard compilations are not based on histological images, and it has been unclear how this might affect the classification abilities of a pre-trained neural network when being used to classify histopathological images. The inventors have recognized and appreciated that using transfer learning to pre-train some portions (e.g., one or more layers) of a deep learning model may reduce computational complexity and training time without significantly sacrificing classification accuracy for some classification problems in the field of cancer image analysis.

The inventors have also recognized and appreciated that a container-based orchestration system may be advantageous for the classification of WSIs using deep learning methods. A container-based orchestration system (e.g., Kubernetes™, Docker™, etc.) can provide efficient deployment of components of an application among available computing resources. Applying a container-based orchestration system to deep learning methods for the classification of WSIs can make the classification process more computationally efficient (e.g., less computationally-resource intensive and/or less time-intensive).

Accordingly, the inventors have developed systems and methods for the use of a container-based orchestration system for deep learning methods of classifying WSIs. Some embodiments include a system for identifying cancerous tissue in a tissue sample, the system includes a processor operatively connected to a memory containing instructions which, when executed by the processor, cause the processor to instantiate a container-based processing architecture. In some embodiments, the container-based processing architecture includes a first container configured to process a WSI of the tissue sample to obtain a processed WSI. In some embodiments, the container-based processing architecture includes a second container configured to provide the processed WSI from the first container as input to a trained deep learning model to obtain feature values output by the trained deep learning model. In some embodiments, the container-based processing architecture includes a third container configured to classify the WSI as either an image of non-cancerous tissue or an image of cancerous tissue based on the feature values output by the deep learning model in the second container.

Some embodiments include a method for identifying cancerous tissue in a WSI of a tissue sample. The method includes processing a WSI of the tissue sample and classifying, using a trained deep learning model, the WSI as being an image of cancerous tissue or an image of non-cancerous tissue. In some embodiments, at least one layer of the trained deep learning model is trained based on a first training data set of histological images (e.g., of a plurality of tissue types). In some embodiments, at least one layer of the trained deep learning model is trained based on a second training data set of non-histological images (e.g., ImageNet or other image training sets).

The inventors have further recognized and appreciated that a deep learning model may be able to identify an underlying genetic mutation associated with a cancerous tumor based on a histopathological image of the tumor. Conventional methods of determining genetic mutations associated with a cancer diagnosis may require expensive and/or time-consuming laboratory methods. Using a trained deep learning model to detect a genetic mutation associated with a cancerous tumor may be faster and cheaper than conventional methods. The inventors have further recognized and appreciated that using a trained deep learning model to detect a genetic mutation associated with a cancerous tumor may provide a method of quickly selecting and administering targeted treatments based on the detected genetic mutations. Accordingly, systems and method for detecting genetic mutations associated with a cancerous tumor, and, then optionally selecting and administering a targeted treatment are provided herein.

Some embodiments include a system for identifying a genetic mutation of a cancerous tissue sample. The system includes a processor operatively connected to a memory containing instructions which, when executed by the processor, cause the processor to instantiate a container-based processing architecture. The container-based processing architecture includes a first container configured to process a WSI of the cancerous tissue sample to obtain a processed WSI. In some embodiments, the container-based processing architecture includes a second container configured to provide the processed WSI from the first container as input to a trained deep learning model to obtain feature values output by the trained deep learning model. In some embodiments, the container-based processing architecture includes a third container configured to classify the WSI as being an image of cancerous tissue having a genetic mutation or an image of cancerous tissue lacking a genetic mutation based on the feature values output by the trained deep learning model in the second container.

Some embodiments include a method for identifying a genetic mutation of a cancerous tissue sample based on a WSI of the cancerous tissue sample. In some embodiments, the method includes processing a WSI of the cancerous tissue sample and classifying, using a trained deep learning model, the at least one WSI as an image of cancerous tissue having a genetic mutation or cancerous tissue lacking a genetic mutation. In some embodiments, the method may further, optionally include selecting a treatment modality based on the classification of the at least one WSI and administering the selected treatment modality to the patient.

Following below are more detailed descriptions of various concepts related to, and embodiments of, techniques for using a deep learning model for classification of histological images. It should be appreciated that various aspects described herein may be implemented in any of numerous ways. Examples of specific implementations are provided herein for illustrative purposes only. In addition, the various aspects described in the embodiments below may be used alone or in any combination, and are not limited to the combinations explicitly described herein.

I. Pan-Cancer Convolutional Neural Networks for Cancer/Non-Cancerous Classification FIG. 1A depicts, schematically, an example of a process 100 of training and testing a deep learning model for classifying WSIs of tissue samples as comprising cancerous or non-cancerous cells, in accordance with some embodiments. Process 100 may be implemented using a suitable computing device (e.g., as described in connection with FIG. 17 herein) or may be performed remotely using a cloud computing platform (e.g., Google Cloud™, Amazon Web Services™, etc.).

In some embodiments, process 100 may be orchestrated using a container-based orchestration system (e.g., Kubernetes™, Docker™, etc.), with each portion of the process 100 being stored and executed in separate containers and data passing between containers. For example, process 100 may be orchestrated using a Kubernetes™ cluster with up to 4000 pods, providing for scalability of the process. Implementing the image processing described herein using such a container-based processing architecture can speed up the processing by a factor of approximately 4000 as compared to serialized implementation because of the parallel nature of the container-based processing architecture. Similar increases in computational speed are also achieved for training and classification testing of the deep learning model. Additionally, the elastic autoscaling of container-based processing architectures enables the implementation of computing resources only when they are needed, resulting in efficient use of the hardware as well as lowering the computing cost by terminating compute instances immediately after they complete.

An example of a WSI is shown in portion 102, where one or more WSIs of tissue samples are input, in accordance with some embodiments. WSIs may be input for training the deep learning model or for classification once the deep learning model has been trained. For training the deep learning model, the WSIs may be sourced from The Cancer Genome Atlas (TCGA). The inventors selected WSIs from the TCGA across 19 tissue types having at least 25 WSIs of non-cancerous tissue, including breast invasive carcinoma (BRCA), kidney renal clear cell carcinoma (KIRC), ovarian cancer (OV), lung squamous cell carcinoma (LUSC), lung adenocarcinoma (LUAD), colon adenocarcinoma (COAD), stomach adenocarcinoma (STAD), uterine corpus endometrial carcinoma (UCEC), head-neck squamous cell carcinoma (HNSC), prostate adenocarcinoma (PRAD), thyroid cancer (THCA), cervical kidney renal papillary cell carcinoma (KTRP), urothelial bladder carcinoma (BLCA), liver hepatocellular carcinoma (LIHC), rectum adenocarcinoma (READ), sarcoma (SARC), pancreatic adenocarcinoma (PAAD), esophageal carcinoma (ESCA), and kidney chromophobe (KICH).

Figure 3A:
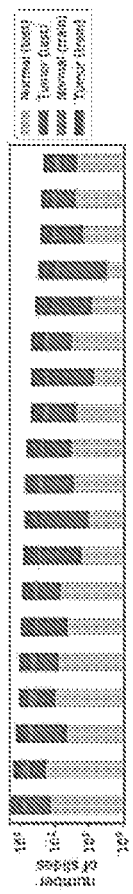
FIG. 3A shows the number of tumor and normal whole slide images (WSIs) used to train and test the deep learning model of FIGS. 1A and 1B, according to some embodiments.

The number of WSIs used to train and test the deep learning model are shown in FIG. 3A for each tissue type described above. Between 205 and 1949 WSIs were selected for use from each tissue type to test and train the deep learning model for classification of WSIs as being of cancerous or non-cancerous tissue. Because of the low number of non-cancerous FFPE WSIs available through the TCGA, flash-frozen WSIs (with barcodes ending with BS, MS, or TS) were preferentially selected for training and testing of the deep learning model.

For training the deep learning model, after inputting the WSIs in portion 102, the set of WSIs may be randomly be divided in portion 104, with 70% of the WSIs being used for training and 30% of the WSIs being used for later testing of the deep learning model's classification abilities. To address the problem of data imbalance, different classes of samples may be undersampled to match the number of samples in the smallest class. To mitigate the effects of label imbalance in classification of cancerous and non-cancerous tissue, undersampling may be performed during training by rejecting inputs from the larger class according to class imbalances, such that, on average, the deep learning model later receives an equal number of cancerous and non-cancerous WSI tiles as input.

After selecting the training and testing data in portion 104, processing of each WSI may be performed in portion 106. For example, each WSI may be tiled into smaller sub-images for input into the deep learning model and individual, per-tile classification, in accordance with some embodiments. The tiles may be selected so that they are non-overlapping within the WSI. The tiles may be 512 by 512 pixels in size, or may be any suitable size. Tiling the WSIs may allow for more efficient forward passes through the deep learning model and/or a spatially-dependent classification of the WSI. Additional pre-processing steps may occur in portion 106, such as background removal (e.g., removal of extraneous pixels not representing tissue cells) and/or a changing of a magnification of the WSIs such that the magnification of all WSIs is consistent within the set of WSIs. In some embodiments, during portion 104 up to 1,000 compute instances and up to 4,000 Kubernetes pods may be used. In some embodiments, the compute instances may each include 8 vCPUs and 52 GB of memory, though it is to be appreciated that additional vCPUS and/or memory may be used in some embodiments. A similar architecture may be implemented for training and testing of the deep learning model, as described herein.

The processed WSIs (e.g., tiles) may then be passed through the deep learning model in a forward pass in portion 108, in accordance with some embodiments. In some embodiments, the deep learning model may be a convolutional neural network (CNN). An exemplary architecture of the deep learning model 120 is shown in more detail in FIG. 1B. In some embodiments, the deep learning model 120 may be an Inception v3 network. In some embodiments, the Inception v3 network may additionally be trained on the WSI training set. However, in some embodiments, the Inception v3 network may be trained using transfer learning (e.g., being pre-trained on nonhistological image collections such as ImageNet) to reduce computational training time and complexity.

In some embodiments, the output of portion 108 may be obtained from the last average pooling layer 121 of the Inception v3 network. The last average pooling layer 121 may include 2048 neurons and may output values in the form of vectors of 2048 floating point values (herein, "caches"). These output caches may be converted and stored in the TFRecord file format in groups of 10,000 in portion 110.

Figure 1B:
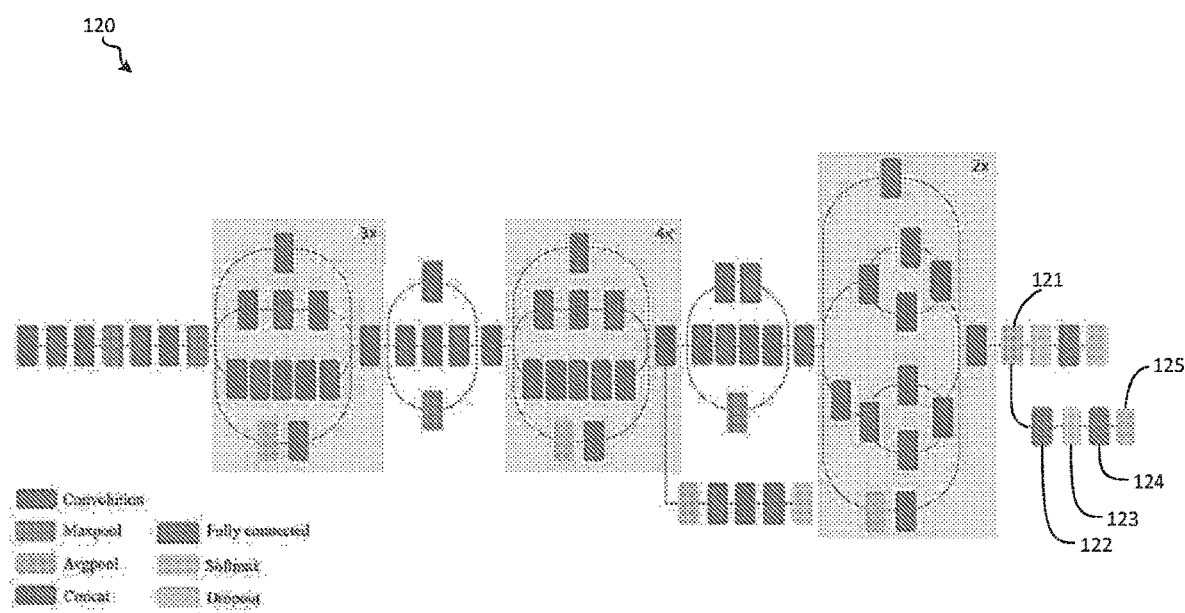
FIG. 1B depicts a deep learning model for performing histopathological image classification as described in connection with FIG. 1A, according to some embodiments.

The stored TFRecord files from portion 110 may be used as input to an additional series of layers shown in the example of FIG. 1B. The additional series of layers includes a first fully-connected layer 122, a dropout layer 123, a second fully-connected layer 124, and a softmax layer 125. The input TFRecord files from portion 110 may be used to train the additional first and second fully-connected layers 122 and 124 in portion 112 separately using the WSI tiles from the TCGA, as described previously. In some embodiments, training simulations may be run for 2000 steps in batches of 512 samples with a 20% dropout rate. In some embodiments, mini-batch gradient descent was performed using the Adam optimizer.

In some embodiments, the first fully-connected layer 122 may include 2048 neurons and the second fully-connected layer 124 may include 1024 neurons. An output of the additional fully-connected layer 124 may calculate a classification value used to classify the tiles as, for example, containing or not containing an image of cancerous tissue. In some embodiments, the solfmax layer 125 may be used to generate class probabilities based on the output of the additional fully-connected layer 124. In some embodiments, the output of the softmax layer 125 may be encoded as a one-hot-encoded vector. Per-tile classification receiver operating characteristic (ROC) curves were calculated based on thresholding softmax probabilities and per-slide classification ROCs were based on voting on maximum softmax probability.

In portion 114, tiles from WSIs classified as a part of the test set may be passed through the deep learning model 120 in order to perform testing and classification. In the example of FIG. 1A, the WSI may be classified per-tile with each tile either being classified as containing cancerous tissue or not containing cancerous tissue based on the classification value output by the deep learning model 120. However, the process 100 of FIG. 1A may be adapted to other WSI classification problems as described herein, including identification of cancer subtype and detection of genetic mutations.

Figure 2:
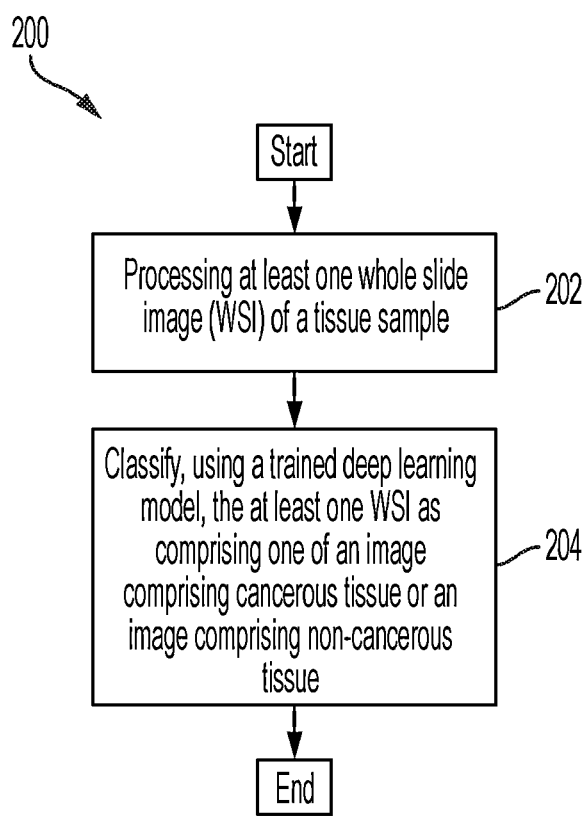
FIG. 2 is a flowchart describing an illustrative process of classifying histopathological images as containing or not containing cancerous tissue, according to some embodiments.

Once the deep learning model 120 is trained, as described in connection with the exemplary process 100 of FIG. 1A, it may be used to classify WSIs as images comprising, for example, cancerous or non-cancerous tissues. FIG. 2 is a flowchart describing an illustrative process 200 for classifying WSIs as images comprising cancerous or non-cancerous tissues, in accordance with some embodiments. The process 200 may be implemented by any suitable computing device as described herein. For example, the process 200 may be implemented using a remote computing device and/or collection of computing devices (e.g., using a cloud computing platform).

Process 200 may begin at act 202, where at least one WSI of a tissue sample may be processed, in accordance with some embodiments. The processing of the WSI may include, for example, splitting of the at least one WSI into a number of tiles and/or removal of background pixels surrounding pixels representing tissue cells, as described in connection with process 100.

Process 200 may then proceed to act 204, in which the processed at least one WSI may be passed to the deep learning model, in accordance with some embodiments. The deep learning model may be, for example, deep learning model 120 as described in connection with FIGS. 1A and 1B herein. The deep learning model may output feature values (e.g., in the form of a vector) that provide information indicative of whether the at least one WSI comprises an image containing cancerous or non-cancerous tissue. The classification, in some embodiments, may be performed either over the entire WSI or on a per-tile basis.

Figure 3B:
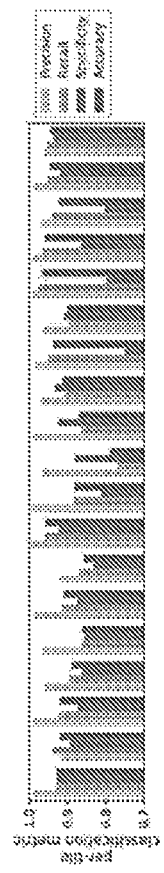
FIG. 3B shows per-tile classification metrics for the deep learning model of FIGS. 1A and 1B, according to some embodiments.

Classification metrics using the training methods and deep learning model of FIGS. 1A and 1B are described in FIGS. 3B-3E. FIG. 3B shows per-tile classification metrics of precision, recall, specificity, and accuracy for test WSIs of each of the 19 tissue types used to train the deep learning model 120. Based on the training approach where all tiles in a normal image are assumed normal and all tiles in a tumor image are assumed tumor, the deep learning model 120 accurately classifies test tiles for most tumor types (accuracy: 0.91±0.05, precision: 0.97±0.02, recall: 0.90±0.06, specificity: 0.86±0.07. Mean and standard deviation calculated across tissue types).

Figure 3C:
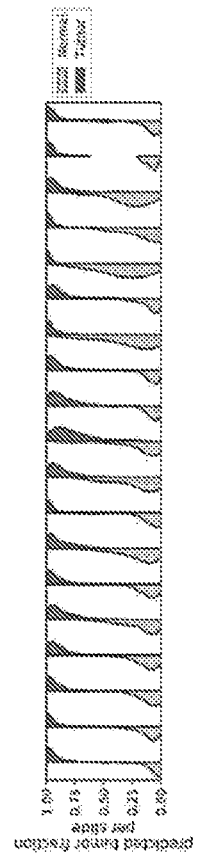
FIG. 3C shows the fraction of tiles within each WSI that were classified as cancerous or non-cancerous by the deep learning model of FIGS. 1A and 1B such that the classification matched the WSI annotation, according to some embodiments.

FIG. 3C shows the predicted fraction of tiles within each WSI that were classified as cancerous or non-cancerous by the deep learning model 120 of FIGS. 1A and 1B, according to some embodiments. The output classification was compared with the WSI annotations provided by the TCGA. The fractions of tiles matching the slide annotation are 0.88±0.14 and 0.90±0.13 for non-cancerous and cancerous samples, respectively. The mean and standard deviation were calculated from all tissue types pooled together. These predicted fractions are large for almost all WSIs, while the tumor-predicted fraction (TPF) is significantly different between cancerous and non-cancerous WSIs (p<0.0001 per-tissue type comparison of cancerous vs. non-cancerous WSIs using Welch's t-test).

Figure 3D:
FIG. 3D shows per-WSI values of area under the curve (AUC) for the receiver operating characteristic (ROC) curve and precision-recall (PR) curve for the deep learning model of FIGS. 1A and 1B, according to some embodiments.
Figure 4:
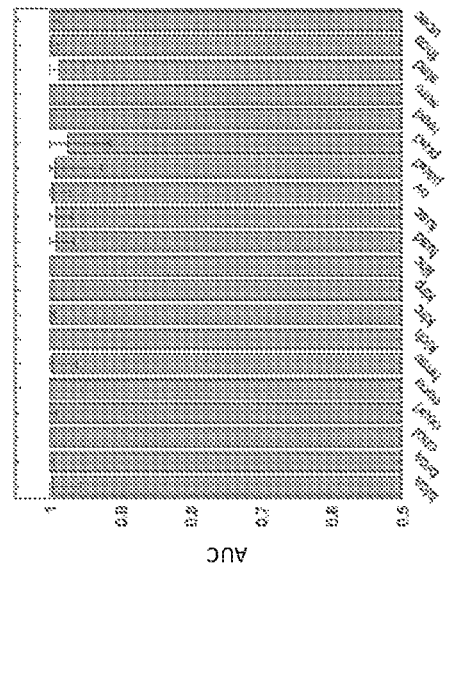
FIG. 4 shows per-slide AUC values for cancerous/non-cancerous classifiers and their confidence intervals where similar tumor types are used for training and testing of the deep learning model of FIGS. 1A and 1B, according to some embodiments.

Classification was also tested on a per-slide basis. FIG. 3D shows per-WSI values of area under the curve (AUC) for the ROC curve and precision-recall (PR) curve for the deep learning model 120 of FIGS. 1A and 1, according to some embodiments. The TPF of each slide was used as a metric to classify the WSI as cancerous or non-cancerous. This approach yielded extremely accurate classification results for all tissue types (mean AUC ROC=0.995, mean PR AUC=0.998). Confidence intervals (CI) of per-slide predictions are given in FIG. 4. The CI lower bound on all classification models was above 90%, with cancer types having fewer slides or imbalanced test data tending to have larger CIs. These results indicate that the deep learning model 120 can successfully classify WSIs as being images of cancerous or non-cancerous tissue across many different tissue types.

Figure 3E:
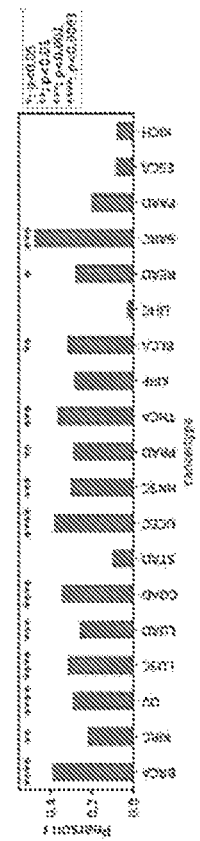
FIG. 3E shows Pearson correlation coefficients between predicted and pathologist evaluation of tumor purity, according to some embodiments.

FIG. 3E shows Pearson correlation coefficients between the TPF obtained from the deep-learning model and pathologist evaluations of tumor purity of the WSIs. More significant positive correlations were found between TPF and TCGA pathologist-reported purity in the majority of cancer types, with larger cohorts tending to have more significant p-values (e.g. BRCA: p=5e-17).

Figure 5:
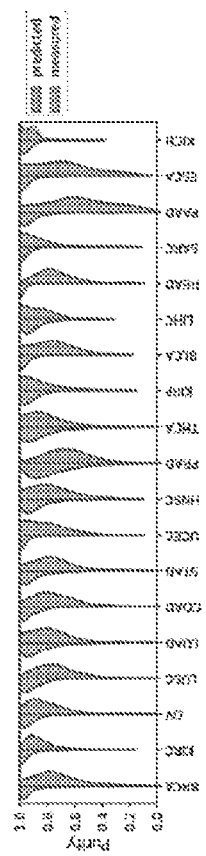
FIG. 5 shows a distribution of tumor purity as predicted by the deep learning model of FIGS. 1A and 1B compared to pathologist reports of tumor purity, according to some embodiments.

FIG. 5 shows a distribution of tumor purity as predicted by the deep learning model of FIGS. 1A and 1B as compared to pathologist measurements of tumor purity. The distributions of TPF were systematically higher than the pathologist annotations, though this difference can be reconciled by the fact that TPF is based on neoplastic area while the pathologist annotation is based on cell counts. Tumor cells are larger than stromal cells and reduce the nuclear density. A notable limitation is the training assumption that tiles in a slide are either all tumor or all normal, as intraslide pathologist annotations are not provided by the TCGA.

II. Neural Network Classification of Cancer Subtypes

The inventors have further recognized that the deep learning model 120 of FIGS. 1A and 1B may be adapted to perform classification of cancer subtypes. In some embodiments, to perform classification of tissue types with more than two cancer subtypes, a multi-class classification may be used with the deep learning model 120 of FIGS. 1A and 1B. To train the deep learning model 120 for this task, WSI images from 10 tissue types were used for subtype classification. FFPE and flash-frozen samples are approximately balanced among the tumor WSIs available from the TCGA, and both were used for subtype classification. Some cancer tissues had subtypes that were available as individual cohorts within TCGA. These 3 tissues were LUAD/LUSC (lung); KICH/KIRC/KIRP (kidney); and UCS/UCEC (uterine). For all other tissues, the TCGA provided single cohorts that spanned multiple subtypes designated by pathologist annotations. The following subtypes were considered: brain (oligoastrocytoma, oligodendroglioma, astrocytoma), breast (mucinous, mixed, lobular, ductal), cervix (adenoma, squamous cell carcinoma), esophagus (adenocarcinoma, squamous cell carcinoma), kidney (chromophobe, clear cell, papillary), lung (adenocarcinoma, squamous cell carcinoma), sarcoma (MFS: myxofibrosarcoma, UPS: undifferentiated pleomorphic sarcoma, DDLS: dedifferentiated liposarcoma, LMS: leiomyosarcomas), stomach (diffuse, intestinal), testis (non-seminoma, seminoma), thyroid (tall, follicular, classical), uterine (carcinoma, carcinosarcoma). Only clinical subtype annotations with at least 15 samples were considered for the task of cancer subtype classification. Samples with ambiguous or uninformative annotations were not included.

Figure 6:
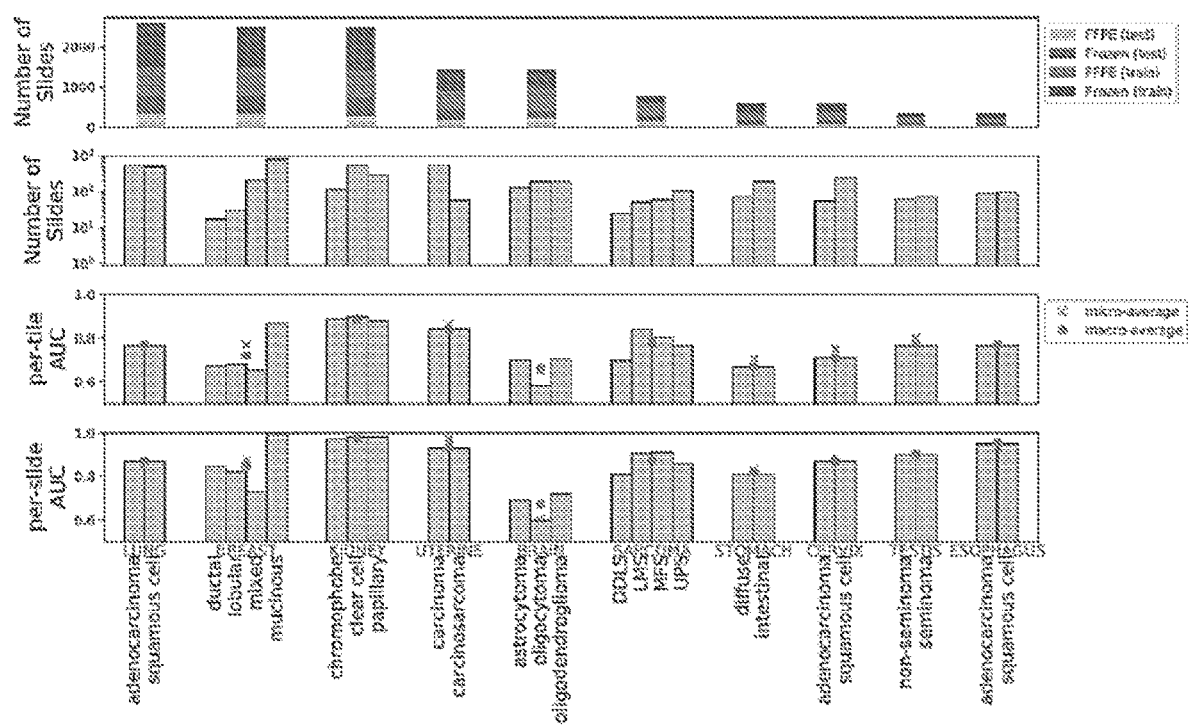
FIG. 6 shows the number of WSIs used for training and testing the deep learning model of FIGS. 1A and 1B while performing classification of cancer subtypes, the number of samples for each cancer subtype, and per-tile and per-slide AUC ROC values for classification of each cancer subtype, according to some embodiments.

FIG. 6A shows the number of WSIs used for training and testing the deep learning model 120 of FIGS. 1A and 1B to perform classification of cancer subtypes, according to some embodiments. FIG. 6B further shows the number of slides that were used for each cancer subtype.

FIGS. 6C and 6D show the per-tile and per-slide classification results, respectively, as AUC ROCs alongside their micro- and macro-averages. At the slide level, the classifiers may identify the subtypes with good accuracy in most tissue types, though generally not yet at clinical precision (AUC micro-average: 0.87±0.1; macro-average: 0.87±0.09). The tissue with the highest AUC micro/macro-average was kidney (AUC 0.98), while the lowest was brain with micro-average 0.60 and macro-average 0.67. All CIs were above the 0.50 null AUC expectation, and all of the AUCs were statistically significant (5% false discovery rate (FDR), Benjamini-Hochberg correction). The individual subtype with largest AUC is the mucinous subtype for breast cancer (adjusted p-value <1e-300). The weakest p-value (adjusted p=0.012) belongs to the oligoastrocytoma subtype of the brain. Slide-level predictions are superior to those at the tile level, though with similar trends across tissues. This indicates that tile averaging provides substantial improvement of signal to noise, consistent with observations for the classification of cancerous and non-cancerous tissues.

III. Cross-Classifications Between Tumor Types Demonstrate Conserved Spatial Behaviors Cross-classification tests show that different tumor types share CNN-detectable morphological features distinct from those in non-cancerous tissues. For each tissue type, the binary classifier of the deep learning model 120 may be re-trained for classifying images as cancerous or non-cancerous using all WSIs in the tissue type cohort. Each tissue type-specific classifier may then be tested to determine its ability to predict whether WSIs of other tissue types contain cancerous or non-cancerous tissues.

Figure 7A:
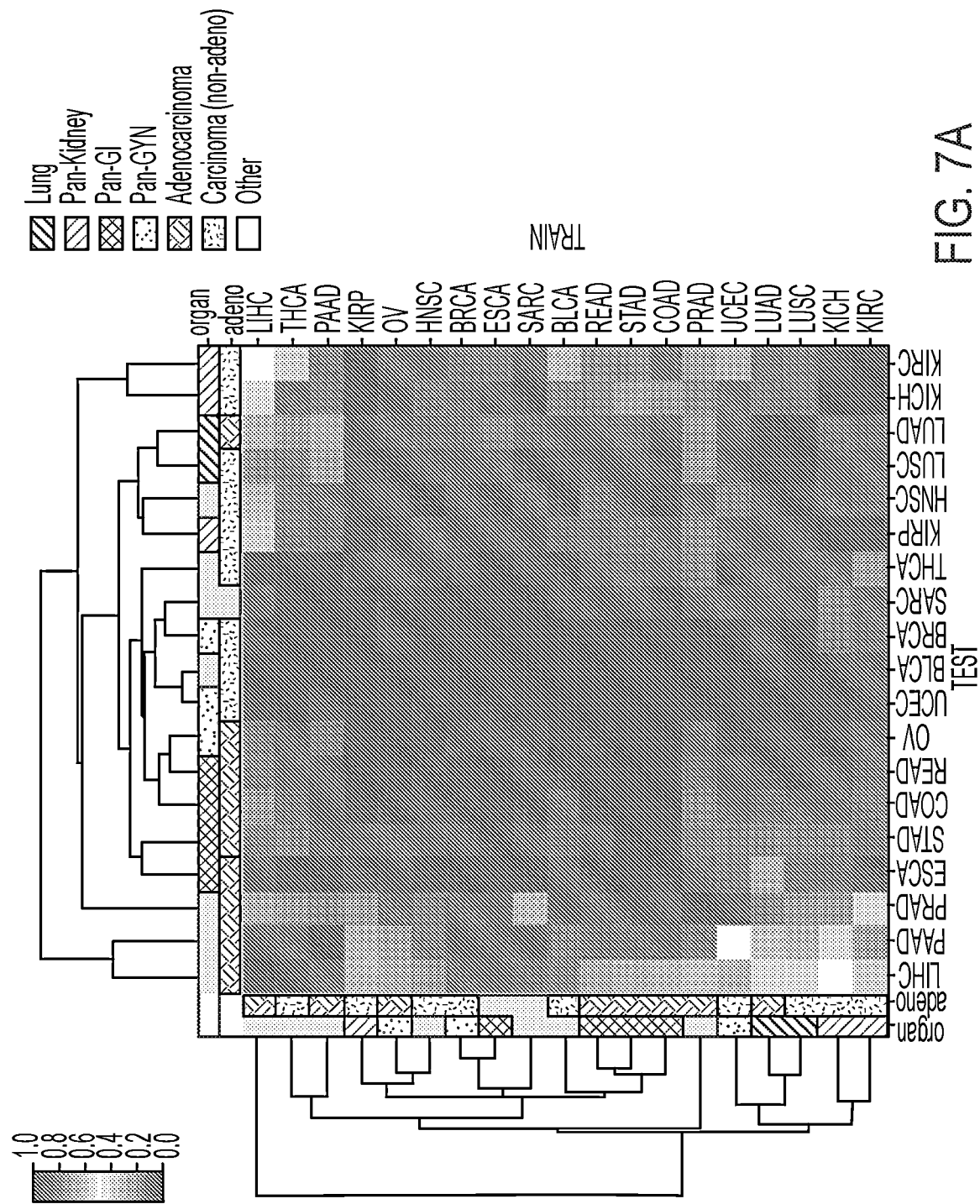
FIG. 7A shows per-slide pairwise AUC values of the deep learning model of FIGS. 1A and 1B when trained on one tissue type and used to classify a different tissue type, according to some embodiments.

FIG. 7A shows a heatmap of per-slide pairwise AUC values of the deep learning model 120 of FIGS. 1A and 1B when trained on one tissue type (vertical axis) and used to classify a different tissue type (horizontal axis), according to some embodiments. The tissue types are hierarchically clustered on the rows and columns of the matrix. Specifically, KIRC/KIRP/KICH were labeled as pan-kidney, UCEC/BRCA/OV were labeled as pangynecological (pan-gyn), COAD/READ/STAD were labeled as pan-gastrointestinal (pan-GI), and LUAD/LUSC were labeled as lung. The hierarchical clustering in FIG. 7A shows that cohorts of similar tissue of origin cluster closer together.

From the data of FIG. 7A, it can be observed that the lung cohort clusters together on both the train and test axes, the pan-GI cohort clusters on the test axis and partially the train axis, and the pan-gyn cohort partially clusters on the test axis. The pan-kidney cohort partially clusters on both the train and test axes. To quantify this, the associations between the proximity of cohorts on each axis was tested and similarity of their phenotype (i.e. tissue of origin/adenoness) was determined. The organ of origin was significantly associated with smaller distances in the hierarchical clustering (p=0.002 for the test axis and p=0.009 for the train axis; Gamma index permutation test, described below).

Hierarchical clustering was applied to cross-classification per-slide AUC values using UPGMA with Euclidean distance. To determine the association between clustering and independent phenotypic labels (i.e. organ and adeno-ness), the Gamma index of spatial autocorrelation from the Python package PySal was used. The Gamma index is defined as:

$$\Gamma = \sum_{i,j} A_{i,j} W_{i,j}$$

where A is the feature matrix and W is the weight matrix, and indices range over cancer cohorts. For each axis and each phenotype group (i.e. organ or adeno-ness), a separate Gamma index was calculated. $A_{i,j}=1$ if cohorts i and j have the same phenotype (e.g both are adenocarcinoma) and $A_{i,j}=0$ otherwise. For weights, $W_{i,j}=1$ if cohorts i and j are immediately clustered next to each other and $W_{i,j}=0$ otherwise. P-values are then calculated by permutation test using the PySal package. Any cohort with the 'Other' phenotype was removed from this analysis. To avoid extensive computation cost for computing CIs, CIs can be computed using the method of Reiser (2000) rather than generating bootstrap subsamples. A similar procedure may be used to compute the CIs of tumor/normal and cancer subtype classifiers. In order to compute tile-level correlations, tumor probability log it may first be computed for each tile, where the tumor probability log it is defined as $\log((p+\varepsilon)/(1-p+\varepsilon))$, where p is the tumor probability and $\varepsilon=0.0001$ is added to avoid dividing by zero or taking a logarithm of zero.

Additionally, cohorts were also grouped by adenocarcinoma/carcinoma status (FIG. 7A, second row from top), though SARC and ESCA do not fit either category. The cohort distances were significantly associated with adeno-ness on the test axis (p-value=0.008). We observed other intriguing relationships among cross-tissue classifications as well. Particularly, Pan-GI created a cluster with Pan-Gyn, supporting these tumor types having shared features related to malignancy. Likewise, Pan-Kidney and lung also cluster close to each other.

Figure 7B:
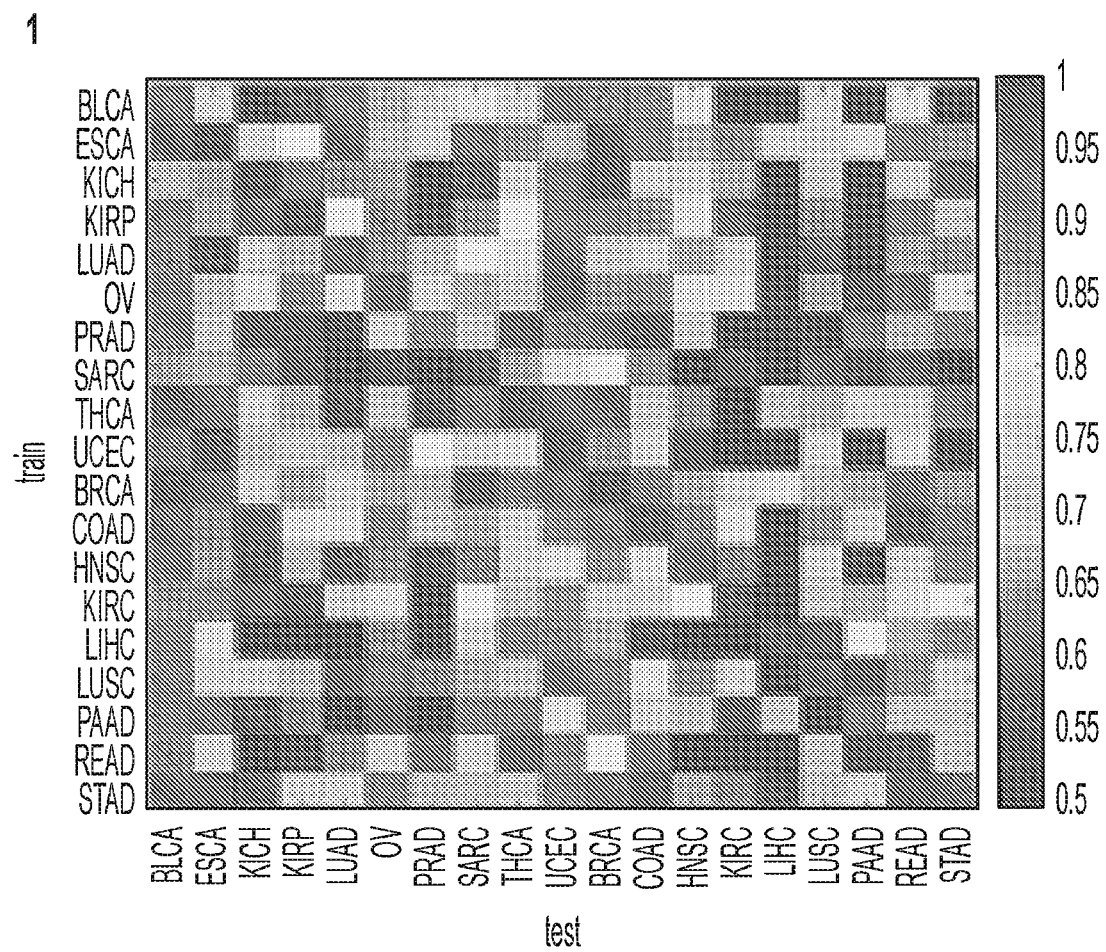
FIG. 7B shows unclustered versions of FIG. 7B, including (1) a lower bound of the confidence interval (CI) of the AUC, (2) the average AUC, (3) an upper bound of the CI of the AUC, (4) the log 10 of the hypothesis tests for the AUC being larger than 0.5, and (5) adjusted p-values of the hypothesis tests for the AUC being larger than 0.5, according to some embodiments.
Figure 7B:
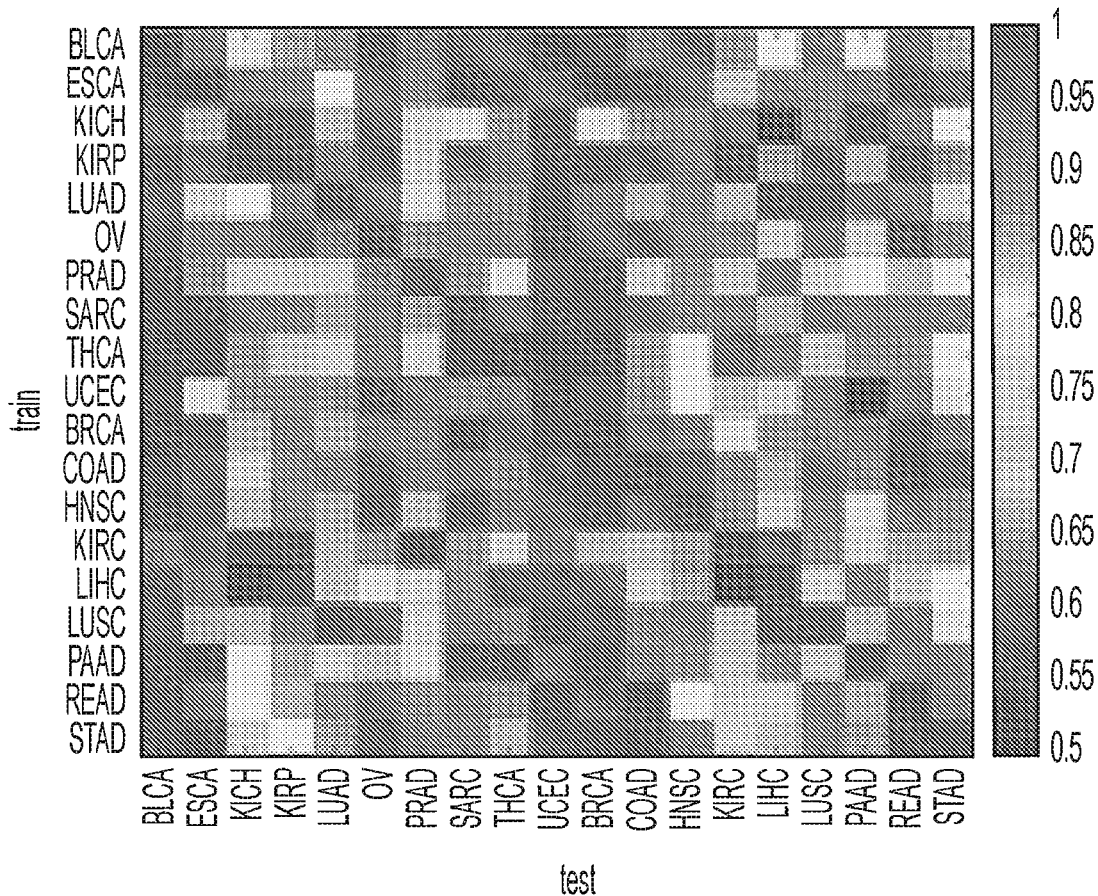
Figure 7B:
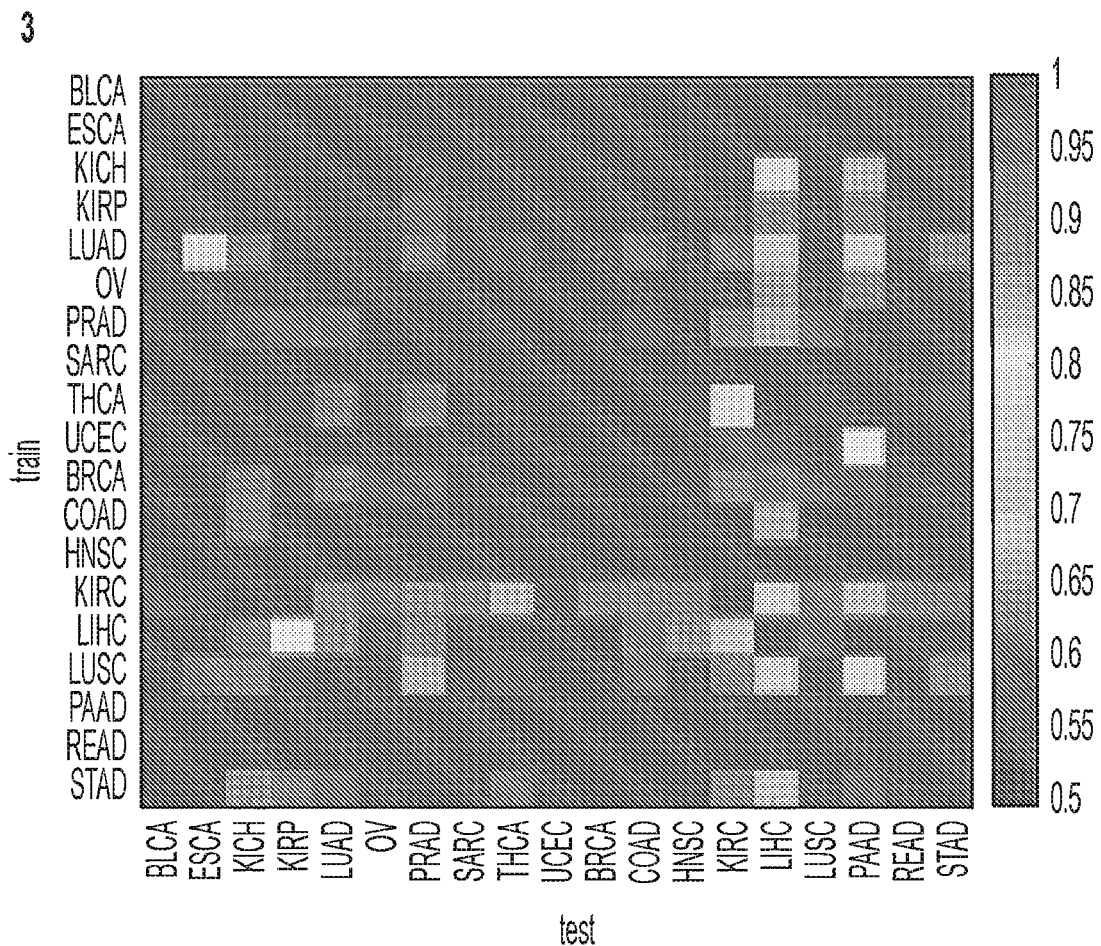
Figure 7B:
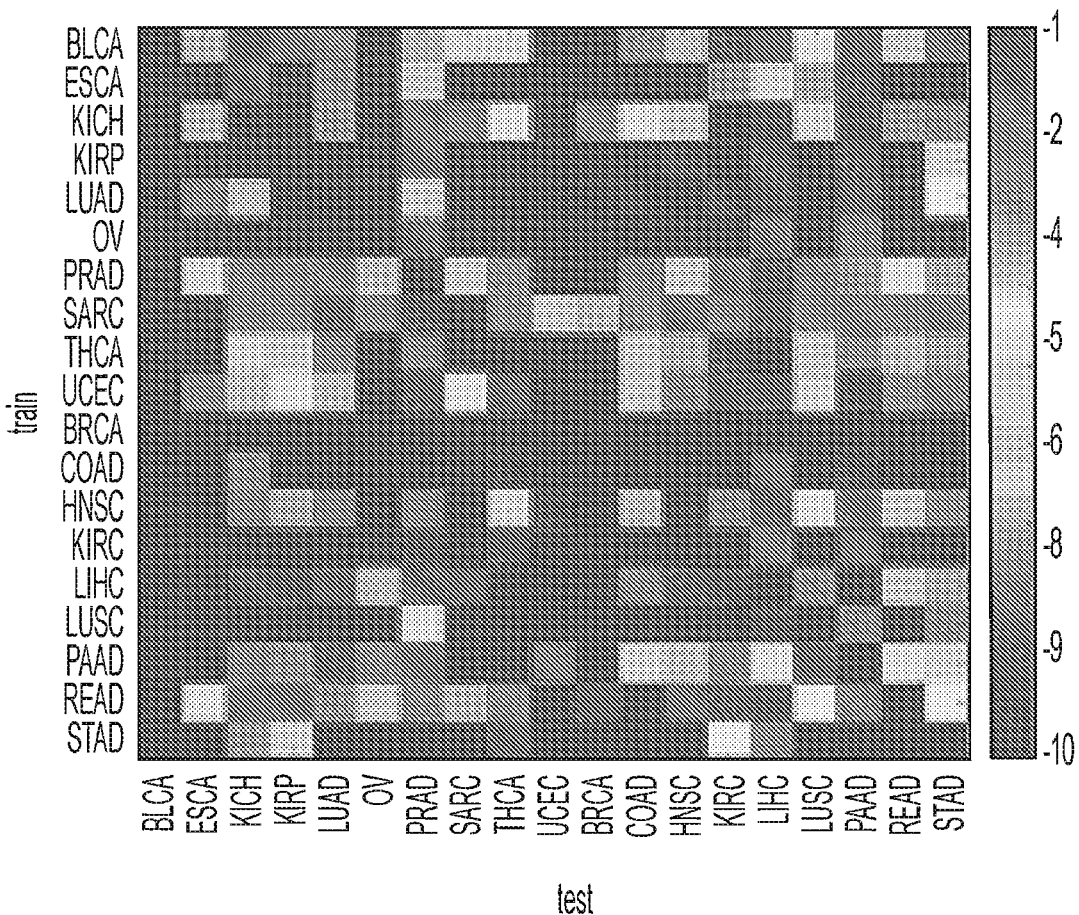
Figure 7B:
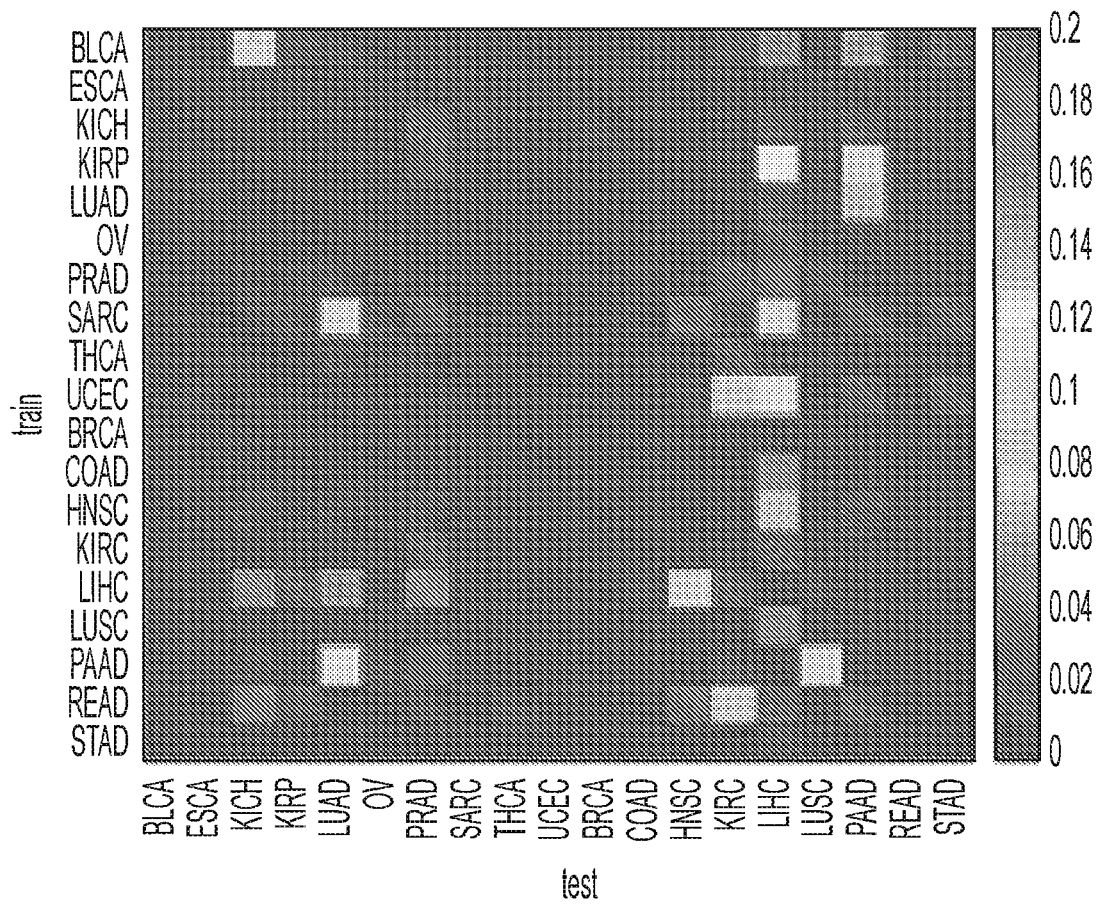

FIG. 7B shows non-clustered versions of FIG. 7A, including 1: lower bounds of the CI of the AUC, 2: the average AUC, 3: upper bounds of the CI of the AUC, 4: the log 10 of the hypothesis tests for the AUC being larger than 0.5, and 5: adjusted p-values of the hypothesis tests for the AUC being larger than 0.5 (null AUC=0.5, alternative AUC>0.5), according to some embodiments. Out of the 361 cross-classification models, the lower bound on the CI of 164 models is above 80%, suggesting the presence of strong common morphological features across various cancer types. Additionally, 330 out the 361 classification models are significant (having AUC>0.5) while bounding the FDR by 5%.

From this data, it should be appreciated that the deep learning model 120, when trained on any single tissue, was successful in classifying WSIs as being of cancerous or non-cancerous tissues in most other tissues (average pairwise AUCs of off-diagonal elements: 0.88±0.11 across all 342 cross-classifications). This prevalence of strong cross-classification supports the existence of morphological features shared across cancer cohorts but not non-cancerous tissues. In particular, classifiers trained on most cohorts successfully predicted cancerous/non-cancerous status in BLCA (AUC=0.98±0.02), UCEC (AUC=0.97±0.03), and BRCA (AUC=0.97±0.04), suggesting that these cancers most clearly display features universal across types. At a 5% FDR, 330 cross-classification AUCs are significant. The AUC mean and CI lower bound are each above 80% for 300 and 164 of these cross-classifications, respectively. A few cancer types, e.g. LIHC and PAAD, showed poor cross-classification to other tumor types, suggesting morphology distinct from other cancers.

To improve spatial understanding of these relationships, the conservation of tile-level predictions was tested between different classifiers, while also analyzing the effect of varying the test set. For each pair of tissue-specific classifiers, a test set of WSIs was specified and the correlation coefficient was then computed of the predicted cancerous/non-cancerous state (e.g., the log it of the tumor probability) across all tiles in the test set. This calculation was repeated for each test set and was indexed by tissue type (breast, bladder, etc.). Each test set included both cancerous and non-cancerous WSIs for the tissue type.

Figure 8A:
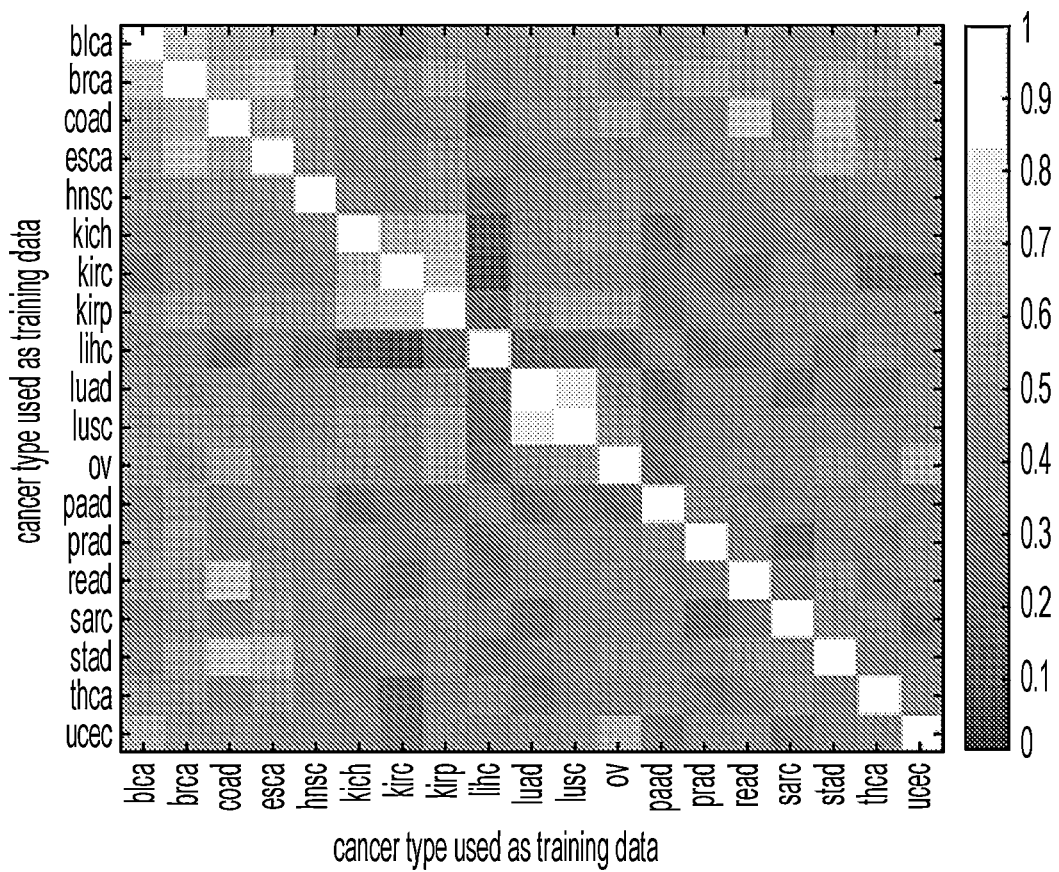
FIG. 8A shows average correlation coefficients between tissue classifiers when both cancerous and non-cancerous WSIs are present in the classification test set of WSIs, according to some embodiments.
Figure 8B:
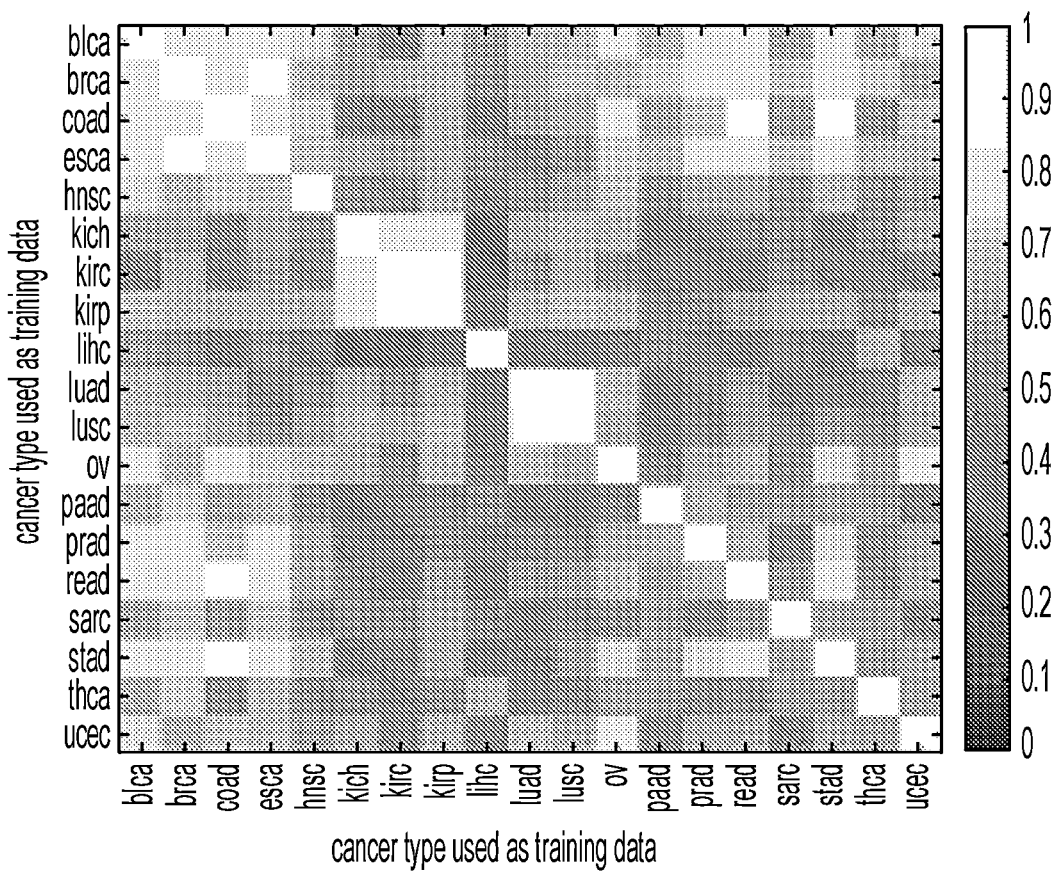
FIG. 8B shows maximum correlation coefficients between tissue classifiers when both cancerous and non-cancerous WSIs are present in the classification test set of WSIs, according to some embodiments.
Figure 8C:
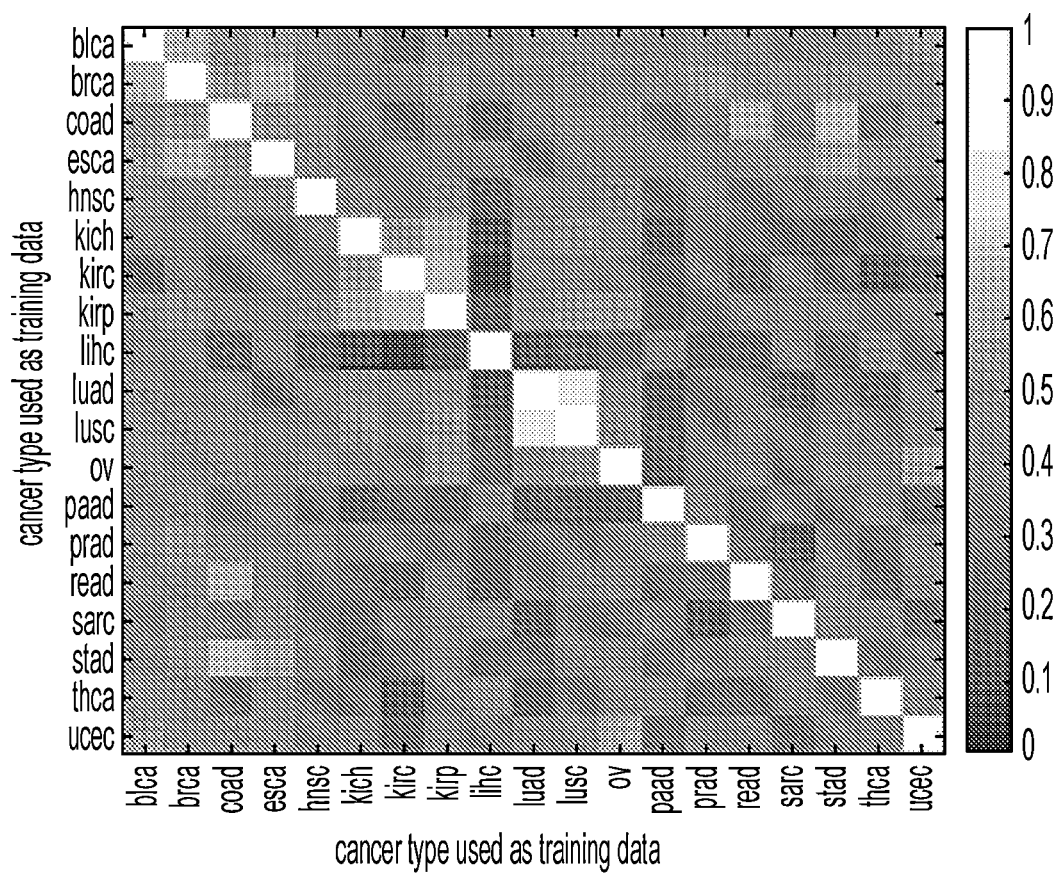
FIG. 8C shows average correlation coefficients between tissue classifiers when only cancerous WSIs are present in the classification test set of WSIs, according to some embodiments.
Figure 8D:
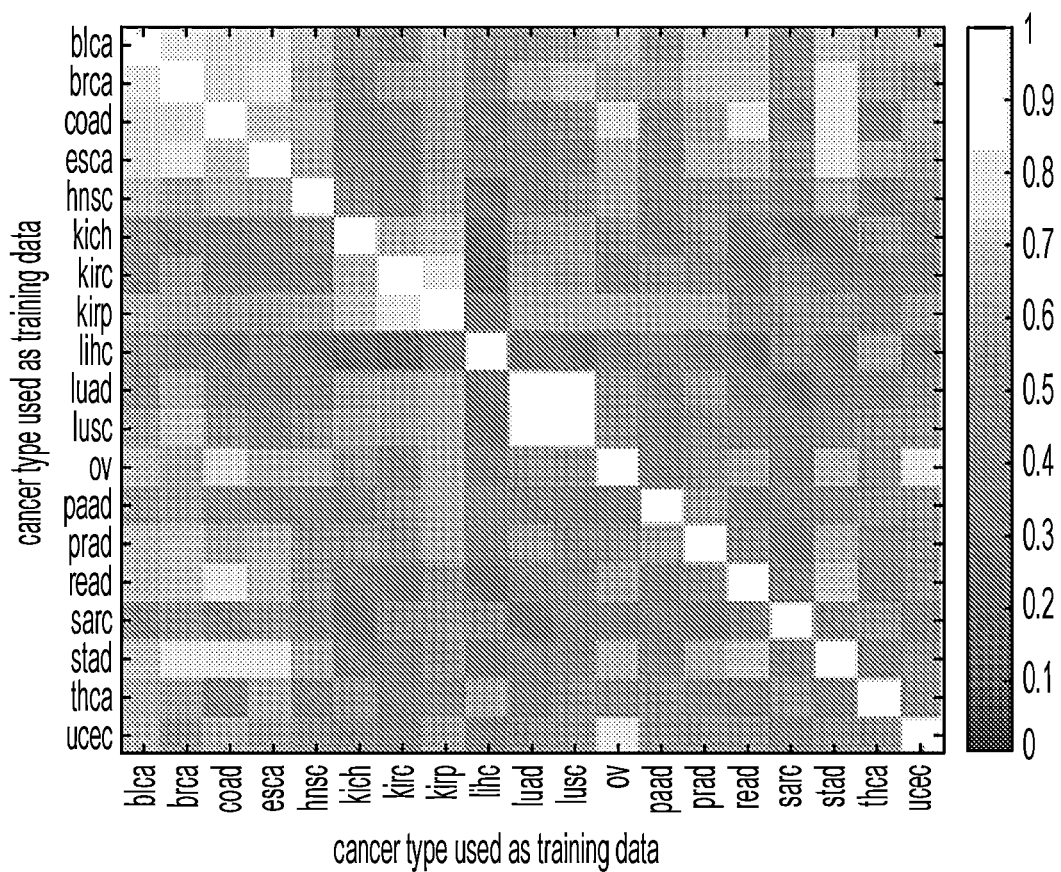
FIG. 8D shows maximum correlation coefficients between tissue classifiers when only cancerous WSIs are present in the classification test set of WSIs, according to some embodiments.

Correlations of predicted tumor/normal status (e.g., the log it of tumor probability as described herein) between pairs of classifiers, specified on the x-axis and the y-axis, are shown in FIGS. 8A through 8D. FIGS. 8A and 8B show for each pair of classifiers the average and maximum correlation coefficients, respectively, over the test sets. Many correlations are positive, with an average and standard deviation over all pairs of classifiers of 45±16% (FIG. 8A, diagonal elements excluded), indicating cross-classifiers agree at the tile level. These tile-level results supported the slide-level results in FIGS. 8C and 8D. FIGS. 8C and 8D are analogous to FIGS. 8A and 8B, but computed only over tumor slides. Classifiers with low cross-classification slide-level AUCs, such as LIHC, had the smallest tile level correlations.

Tile-level predictions also showed similarities between classifiers derived from the same tissue (e.g. LUAD-LUSC, KICH-KIRP-KIRC). Similarities between classifiers became even more apparent when the test tissue with the strongest correlation for each pair of classifiers was focused on (FIG. 8B). These positive correlations are not simply due to distinguishing tiles in tumor slides from tiles in normal slides but rather reflect the biology within cancerous tissue images.

Based on this information, it may be appreciated that certain tissue types might be particularly easy to classify, and to test this the tissue sets that yielded the maximal correlations for each pair of classifiers in FIG. 8B were tabulated. For each pair, the 3 tissue sets yielding the highest correlations were listed. If this were random, each tissue would be expected to appear in this list 27 times. However, an extreme prevalence for BRCA (132 appearances, p=8.5e-119), BLCA (106 appearances, p=2.5e-43), and UCEC (62 appearances, p=1.9e-11) was observed. Many classifier pairs agree better within these 3 tissues than they do within their training tissues. Thus BRCA, BLCA, and UCEC may be considered canonical types for intraslide spatial analysis, in addition to their high cross-classifiability at the whole slide level (e.g., as indicated by FIG. 7A).

IV. Comparisons of Neural Networks for TP53 Mutation Classification

Figure 9A:
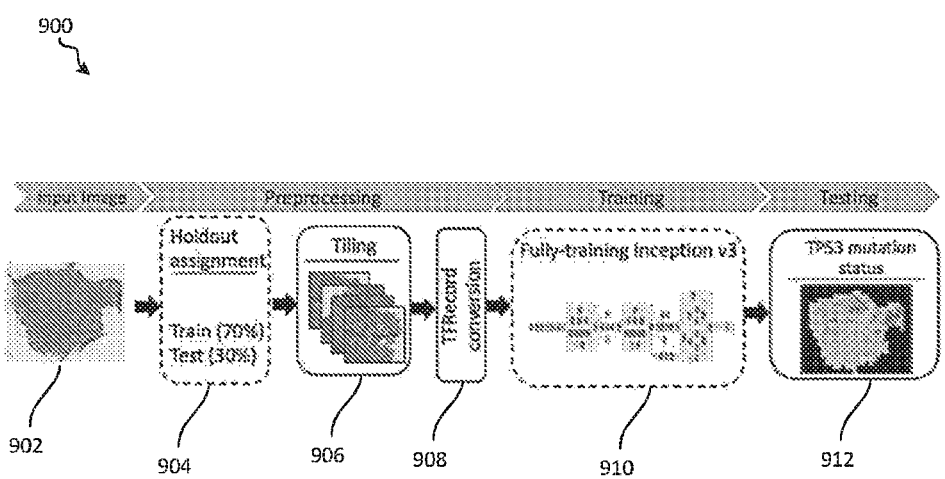
FIG. 9A depicts, schematically, a system for performing classification of genetic mutations of tumors in histopathological images using a container-based processing architecture and a deep learning model, according to some embodiments.

The inventors have further recognized and appreciated that a deep learning model may be used to identify an underlying genetic mutation associated with a cancerous tumor based on a histopathological image of the tumor. FIG. 9A depicts, schematically, a process 900 for performing classification of genetic mutations of tumors in histopathological images using a container-based processing architecture and a deep learning model, according to some embodiments.

Process 900 may be implemented using a suitable computing device (e.g., as described in connection with FIG. 17 herein) or may be performed remotely using a cloud computing platform (e.g., Google Cloud™, Amazon Web Services™, etc.). In some embodiments, process 900 may be orchestrated using a container-based orchestration system (e.g., Kubernetes™, Docker™, etc.), with each portion of the process 900 being stored and executed in separate containers and data passing between containers. For example, process 900 may be orchestrated using a Kubernetes™ cluster with up to 4000 pods, providing for scalability of the process.

An example of a WSI for testing or training the deep learning model for genetic mutation classification is shown in portion 902, where one or more WSIs of tissue samples are input, in accordance with some embodiments. For training the deep learning model, the WSIs may be sourced from, for example, The Cancer Genome Atlas (TCGA). To investigate how images can be used to distinguish cancer drivers, the deep learning model's accuracy for classifying TP53 mutation status was tested in 5 TCGA tissue types (BRCA, LUAD, STAD, COAD and BLCA). These tissue types were chosen due to their high TP53 mutation frequency (Cancer Genome Atlas Research Network 2014a; Cancer Genome Atlas Network 2012; Cancer Genome Atlas Research Network 2014b), providing sufficient testing and training sets for cross-classification analysis. However, it may be appreciated that other genetic mutations and/or combinations of tissue types may be selected for genetic mutation classification.

As an illustrative example of genetic mutation classification, flash-frozen WSIs of BRCA, LUAD and STAD tissue types were chosen for training and testing of the deep learning model. Impactful TP53 mutations were determined using masked somatic mutations maf files called by MuTect2. Mutations which were categorized as MODERATE/HIGH (e.g., by VEP software) in the IMPACT column were considered as impactful mutations. If the gene had at least one impactful mutation in the sample, it was counted as mutated, but was considered as wild-type otherwise. Table 1 shows the number of wild type and mutated slides in each tissue type. For cross-classification, the deep learning model was trained on the entire training cohort (e.g., across tissue types) and predictions were made on the entire test cohort.

TABLE 1

| Cancer Type | Number of Wild Type Slides | Number of Mutated Slides |
|---|---|---|
| BRCA | 647 | 338 |
| LUAD | 295 | 270 |
| STAD | 237 | 200 |
| BLCA | 217 | 194 |
| COAD | 184 | 214 |

For training the deep learning model, after inputting the WSIs in portion 902, the set of WSIs may be randomly be divided in portion 904, with 70% of the WSIs being used for training and 30% of the WSIs being used for later testing of the deep learning model's genetic mutation classification abilities. To address the problem of data imbalance, different classes of samples may be undersampled to match the number of samples in the smallest class. To mitigate the effects of label imbalance in classification of cancerous and non-cancerous tissue, undersampling may be performed during training by rejecting inputs from the larger class according to class imbalances, such that, on average, the deep learning model later receives an equal number of cancerous and non-cancerous WSI tiles as input.

After selecting the training and testing data in portion 904, processing of each WSI may be performed in portion 906. For example, each WSI may be tiled into smaller sub-images for input into the deep learning model and individual, per-tile classification, in accordance with some embodiments. The tiles may be selected so that they are non-overlapping within the WSI. The tiles may be 512 by 512 pixels in size, or may be any suitable size. Tiling the WSIs may allow for more efficient forward passes through the deep learning model and/or a spatially-dependent classification of the WSI. Additional pre-processing steps may occur in portion 906, such as background removal (e.g., removal of extraneous pixels not representing tissue cells) and/or a changing of a magnification of the WSIs such that the magnification of all WSIs is consistent within the set of WSIs. In some embodiments, during portion 906 up to 1,000 compute instances and up to 4,000 Kubernetes pods may be used. In some embodiments, the compute instances may each include 8 vCPUs and 52 GB of memory, though it is to be appreciated that additional vCPUS and/or memory may be used in some embodiments. A similar architecture may be implemented for training and testing of the deep learning model, as described herein.

Figure 9B:
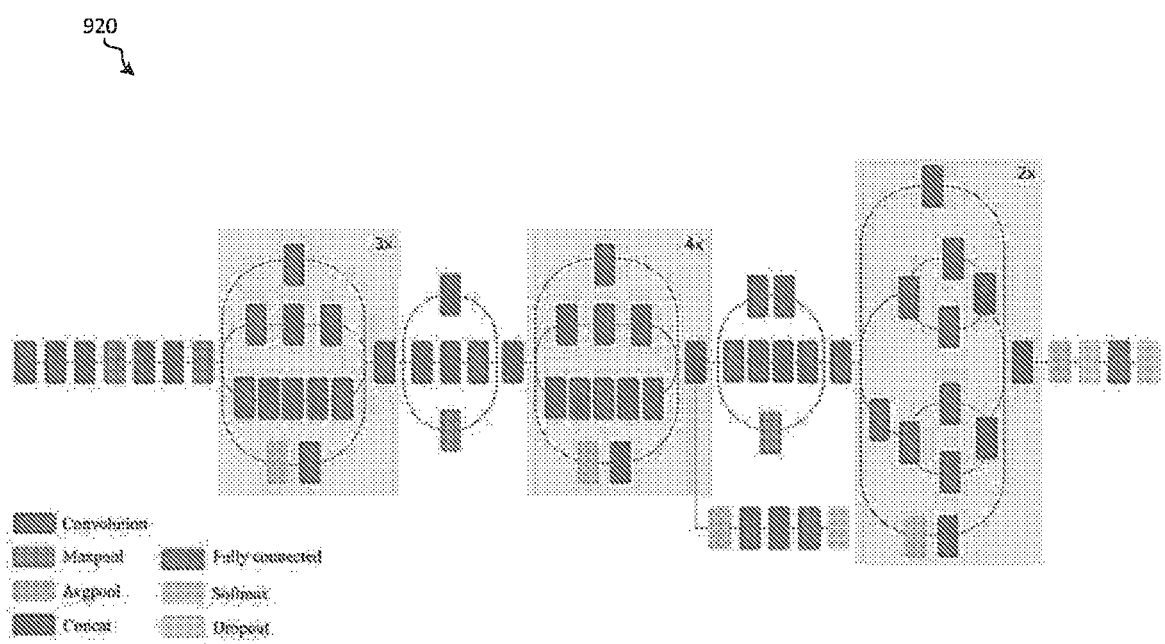
FIG. 9B depicts a deep learning model classification of genetic mutations of tumors in histopathological images as described in connection with FIG. 9A, according to some embodiments.

The WSI tiles may be converted and stored in the TFRecord file format in portion 908. The stored TFRecord files from portion 908 may then be used as input to the deep learning model in portion 910 to obtain output feature values from the deep learning model. The deep learning model may be, for example, a CNN in some embodiments. As depicted in FIG. 9B, the deep learning model 920 for classification of genetic mutations of tumors in WSIs may be an Inception v3 network.

In some embodiments, the deep learning model 920 may be fully-trained on WSIs of cancerous and non-cancerous tissues. Using transfer learning (e.g., pre-training part or all of deep learning model 920 on non-histological images), moderate to low AUCs for TP53 mutation/wild type classification were obtained (0.66 for BRCA, 0.64 for LUAD, 0.56 for STAD, 0.56 for COAD, and 0.61 for BLCA). Due to this relatively weak performance using non-histological images as a training set, it may be desirable to switch to the more computationally-intensive approach in which all parameters of the deep learning model 920 may be trained using WSIs.

After passing the tiled WSIs through the deep learning model 920 in portion 910, feature values output from the deep learning model 920 may be passed to portion 912, where genetic mutation classification may be performed in some embodiments. To predict mutations in the TP53 gene, 2-way classifiers in portion 912 may also be trained based on the input training and test WSI sets. These 2-way classifiers may be configured to output a classification value indicating whether a WSI and/or WSI tile comprise an image of a cancerous tissue having or not having a genetic mutation.

Figure 10:
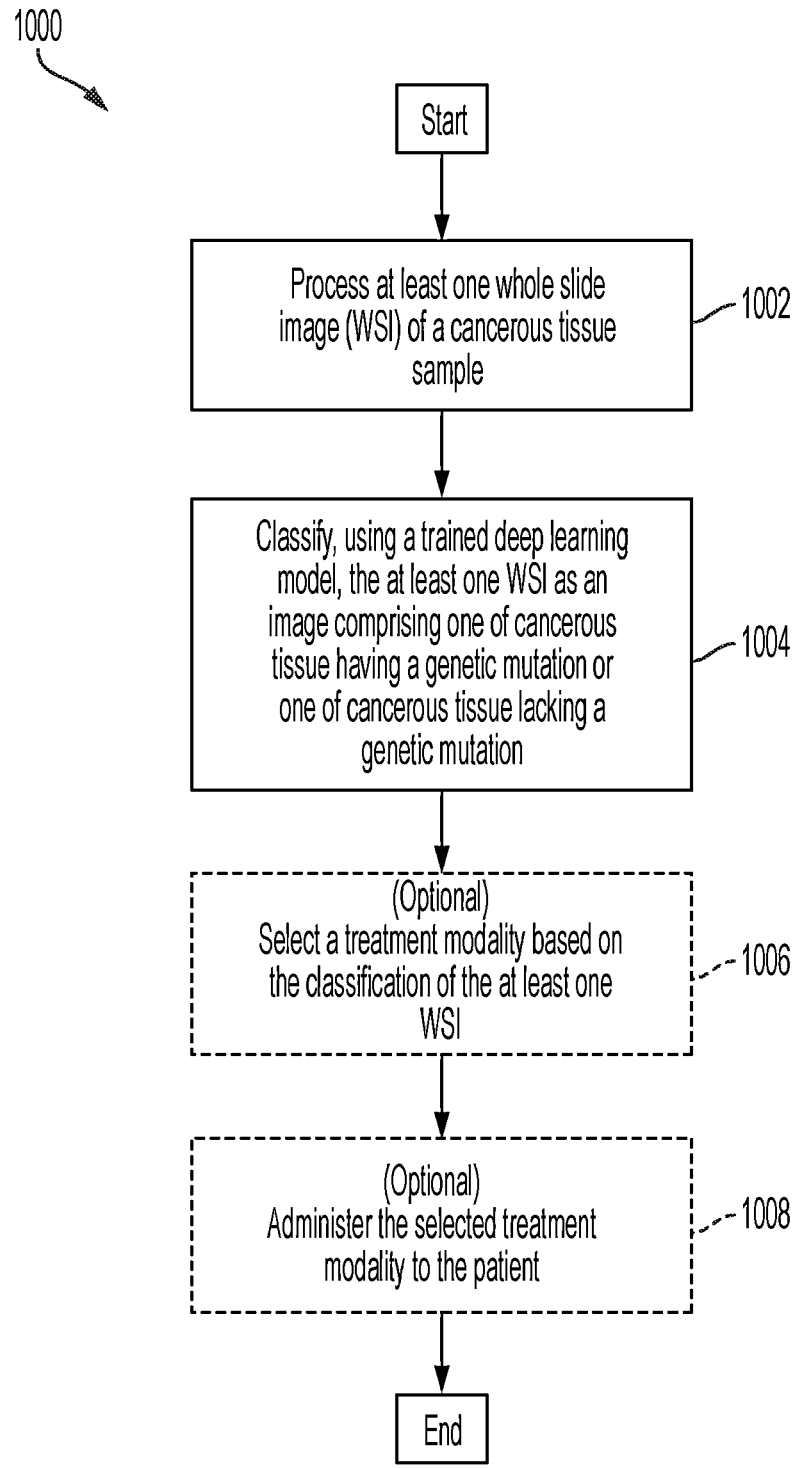
FIG. 10 is a flowchart describing a process of classifying histopathological images, using a trained deep learning model, as containing or not containing cancerous tissue with a genetic mutation and optionally treating a patient based on the classification, according to some embodiments.

FIG. 10 is a flowchart describing a process of classifying WSIs, using a trained deep learning model, as containing or not containing cancerous tissue with a genetic mutation and optionally treating a patient based on the classification, according to some embodiments. The process 1000 may be implemented by any suitable computing device as described herein (e.g., with connection to FIG. 17). For example, the process 1000 may be implemented using a remote computing device and/or collection of computing devices (e.g., using a cloud computing platform).

Process 1000 may begin at act 1002, where at least one WSI of a cancerous tissue sample may be processed. Act 1002 may be performed, for example, in accordance with portion 906, as described in connection with FIG. 9A. For example, each WSI may be tiled into smaller sub-images for input into the deep learning model and individual, per-tile classification, in accordance with some embodiments. The tiles may be selected so that they are non-overlapping within the WSI. The tiles may be 512 by 512 pixels in size, or may be any suitable size. Additional pre-processing steps may occur in portion 906, such as background removal (e.g., removal of extraneous pixels not representing tissue cells) and/or a changing of a magnification of the WSIs such that the magnification of all WSIs is consistent within the set of WSIs.

Process 1000 may then proceed to act 1004, where the at least one WSI may be classified as an image comprising one of cancerous tissue having a genetic mutation or one of cancerous tissue lacking a genetic mutation, according to some embodiments. The classification may be performed by a trained deep learning model. For example, the classification may be performed by deep learning model 920, as described in connection with FIGS. 9A and 9B herein.

Optionally, after act 1004, process 100 may proceed to act 1006, where a treatment modality may be selected based on the classification of the at least one WSI as being an image of cancerous tissue having or not having a genetic mutation, in accordance with some embodiments. For example, a WSI of breast cancer tissue may be classified as being an image of breast cancer tissue having a HER2 amplification mutation or as being an image of breast cancer tissue not having a HER2 amplification mutation. Based on this classification, a treatment modality of using trastuzumab as a part of treating the HER2-amplified breast cancer may be selected. It may be appreciated that the deep learning model may be trained to classify WSIs as containing one of many genetic mutations, not simply TP53 or HER2 genetic mutations. As a result, the treatment modality may include one or more medications, alone or in combination, selected from among a non-limiting list including: dabrafenib, trametinib, gefitinib, crizotinib, lapatinib, everolimus, anastrozole, olaparib, cisplatin, fluorouracil (5FU), trastuzumab, dasatinib, bevacizumab, bosutinib, ponatinib, leuprorelin, vemurafenib, eribulin, liposomal doxorubicin, fulvestrant, mitoxantrone, nab-paclitaxel, navelbine, idarubicin, mifamurtide, temozolomide, carmustine, amsacrine, amsideine, asparaginase, cerubidin, cytosine arabinoside, daunorubicin, inotuzumab, ozogamicin, acelumab, bexarotene, brentuximab, nelarabine, cetuximab, cisplatin, and/or docetaxel.

After selecting a treatment modality in act 1006, the process may proceed to act 1008, where the selected treatment modality may be administered to the patient, according to some embodiments. Administration may be performed in any suitable manner, in accordance with the selected treatment modality's recommended usage, including but not limited to intravenous administration or oral administration of the treatment to the patient.

Figure 11:
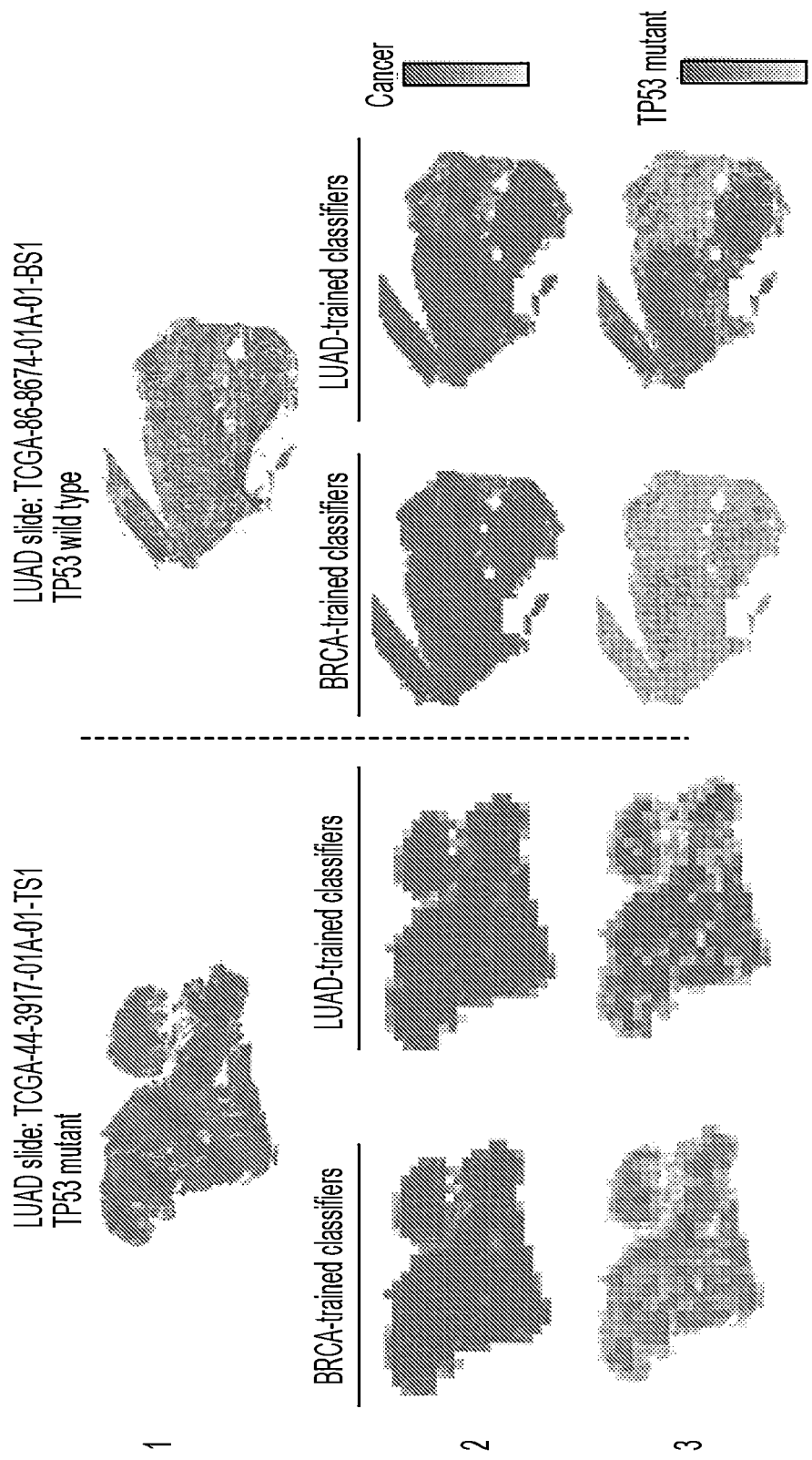
FIG. 11 shows two lung adenocarcinoma (LUAD) WSIs, their classification as cancerous tissue according to breast invasive carcinoma (BRCA) and LUAD-trained classifiers, and the per-tile classification of TP53 genetic mutations, according to some embodiments.

FIG. 11 shows two LUAD WSIs, left and right (row 1), and their classification as cancerous tissue according to BRCA- and LUAD-trained classifiers (row 2), and the per-tile classification of TP53 genetic mutations (row 3), according to some embodiments. The LUAD WSIs include a TP53 mutant tissue (left) and a wild type tissue (right). Row 2 shows prediction maps for these two slides using cancerous and non-cancerous classifiers trained on BRCA and LUAD samples (e.g., as in process 100 described in connection with FIGS. 1A and 1B). Darker colors within the heatmaps indicate cancer classification within the WSIs of row 2. Both models successfully classify samples as cancer and predict similar heatmaps. Row 3 shows prediction maps for these WSIs using TP53 mutation classifiers trained on BRCA and LUAD WSIs (e.g., as in process 900 described in connection with FIGS. 9A and 9B). Darker colors indicate TP53 mutant classification within the WSIs of row 3. The BRCA- and LUAD-trained heatmaps are similar, suggesting that there are spatial features for TP53 mutation that are robust across tumor types. Importantly, the cancerous/non-cancerous classifier and the TP53 mutant/wild type classifier highlight different regions, indicating these classifiers are utilizing distinct spatial features within the WSIs.

Figure 12A:
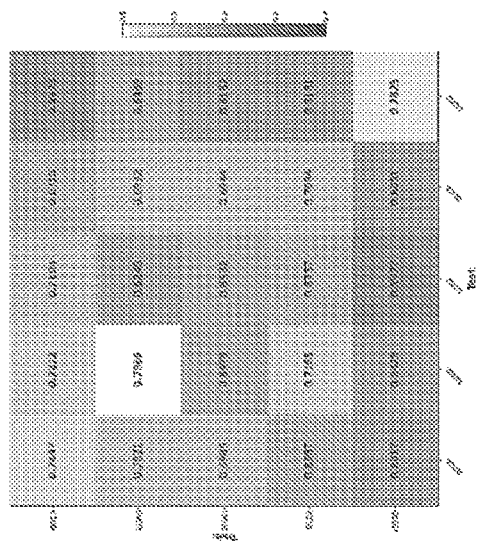
FIG. 12A shows a per-slide classification of TP53 mutation status for five cancer types, according to some embodiments.
Figure 12B:
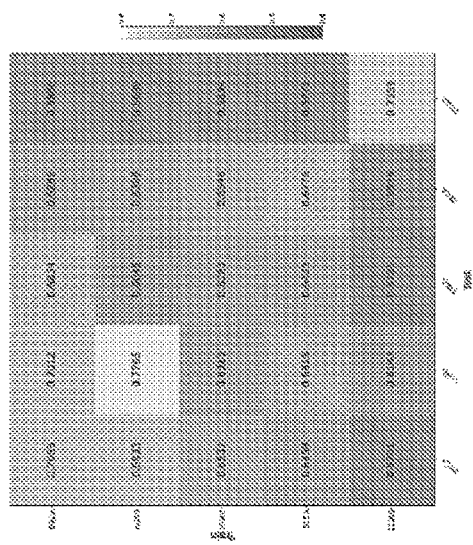
FIG. 12B shows a per-tile classification of TP53 mutation status for five cancer types, according to some embodiments.
Figure 13:
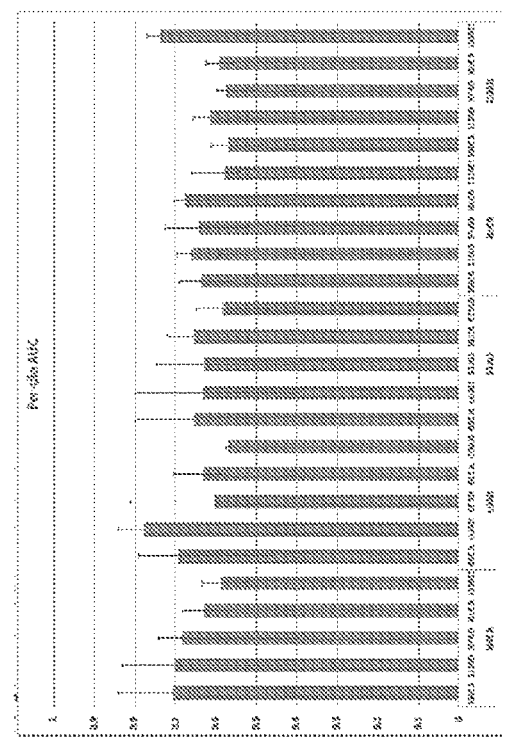
FIG. 13 shows per-tile AUC values for TP53 mutational status cross-classification experiments, according to some embodiments.
Figure 14:
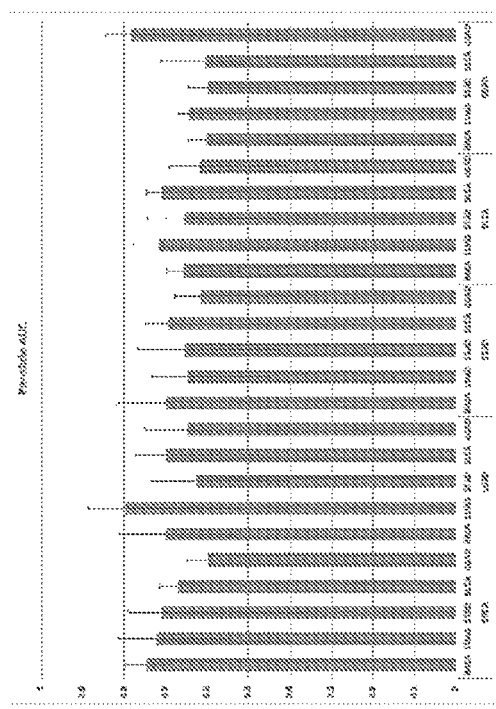
FIG. 14 shows per-slide AUC values for TP53 mutational status cross-classification experiments, according to some embodiments.

Extending these cross-classifications further, FIGS. 12A and 12B show per-slide and per-tile cross- and self-classification AUC values (with 95% CIs), respectively, for TP53 mutation status for five cancer types including BRCA, LUAD, BLCA, COAD, and STAD, according to some embodiments. The numerical values and their CIs of these cross-classification experiments are further shown in FIGS. 13 and 14. FIG. 13 shows per-tile AUC values and CIs for TP53 mutational status cross-classification experiments, and FIG. 14 shows per-slide AUC values and CIs for TP53 mutational status cross-classification experiments.

Cross-predictions yielded AUC values with a comparable range as the self-cohort analyses (AUCs 0.62-0.72 for slides; 0.60-0.70 for tiles), though self-cohort analyses were slightly more accurate. Self-cohort predictions (diagonal values) have AUC values ranging from 0.65-0.80 for per-slide and 0.63-0.78 for per-tile evaluations. Stomach adenocarcinoma (slide AUC=0.65) was notably more difficult to predict than lung adenocarcinoma (slide AUC=0.80), for which AUC values were found to be comparable to the AUC=0.76 LUAD results reported by Coudray et al. (2018). This LUAD fully-trained network (AUC=0.76) outperformed the transfer learning for the same data (AUC=0.64). Colon adenocarcinoma AUC values tended to be low as both a test and train set, suggesting TP53 creates a different morphology in this tissue type. Overall, the positive cross-classifiabilities support the existence of shared TP53 morphological features across tissues.

Figure 15:
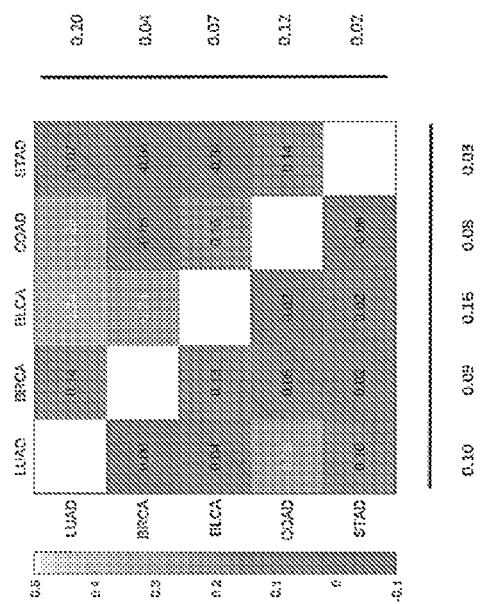
FIG. 15 shows correlation coefficients between a first tissue type used to train the deep learning model in a first instance and a second tissue type associated with the test WSI and the tissue type used to train the deep learning model in a second instance, according to some embodiments.

Next, a tile-level cross-classification analysis was performed as a function of test set. For most test cancer types, little correlation was observed when comparing networks trained on cancers "A" and "B" applied to test cancer "C". Therefore, cases where C is the same as B were focused on. FIG. 15 plots the correlations of TP53 mutation probability log its across cancer pairs, where each row denotes the cancer type the first CNN is trained on, and each column is both the test tissue and the second CNN training tissue. In these cases the correlation coefficients were generally positive and met statistical significance though with moderate magnitude. All correlations were significant except for the BRCA TP53 classifier applied to LUAD tumors (t-test on Fisher z-transformed correlation coefficients, FDR 5%). Notably, classifiers based on LUAD, BRCA, and COAD, worked well on BLCA, BLCA, and COAD tumors, respectively. BLCA and LUAD are the two test cancers with the largest correlations (column average). LUAD and COAD are the two training cancers with the largest correlations (row average). The high row and column averages for LUAD indicate it is canonical both as a test and a training set. Interestingly, the correlations of FIG. 15 are not symmetric. For example, the network trained on LUAD achieves a correlation of 0.34 on BLCA, while the network trained on BLCA has a correlation of 0.04 when tested on LUAD.

Comparisons of classifiers support the existence of morphological features shared across cancer types, as many cross-cancer predictors achieve high AUCs. Specific relationships between types are also informative. Cancers from a common tissue, such as (KIRC, KIRP, KICH), (LUAD, LUAC), and pan-GI cancers are good predictors of each other, and there are also significant similarities within adenocarcinomas and carcinomas, respectively. Interestingly, this behavior is not symmetric between train and test cancer types. For example, while the network trained on KIRC achieves an AUC>90% when tested on BLCA, training on BLCA and testing on KIRC results in an AUC<65%.

V. Features Impacting Tumor Purity Prediction

The TCGA provides annotations only at the whole slide level, limiting the ability to build classifiers that resolve predictive features at the tile level. To better investigate features, datasets with higher resolution annotations were obtained (e.g., BreCaHAD) which provides nucleus-level tumor/normal annotations of 162 TCGA breast cancer ROIs, and 8 colorectal ROIs hand-annotated at nuclear resolution (>18,000 cells). These annotations provide exact tumor purity (the fraction of tumor cells, aka cellular malignancy) in all tiles. A deep learning model may be trained on these tile values, randomly splitting the BreCaHAD dataset into 150 train and 12 test ROIs (a total of >23,000 cells) and using the colorectal set for validation. Purities of the colorectal tiles (512×512 pixels) are spread over a wide range (mean 58%, standard deviation 19.2%), while BreCaHAD purities are higher (mean 87% in the training set), as detailed in FIG. 16. These nucleus-based CNNs yielded mean absolute error of 14% and 15% for the test breast and colorectal sets, respectively. Root mean squared error (RMSE) values were 8% and 20%, respectively. Although the deep learning model was trained only on breast data, the average prediction for the colorectal datasets (69%) was shifted toward the true colorectal mean, suggesting that the deep learning model is able to learn some features common between breast and colorectal tumors.

Purity estimates were tested to determine if they were due only to local information around each cell nucleus or whether other image properties were informative. For this a classifier designed to predict cancerous/non-cancerous status from individual nucleus images was evaluated. The classifier was trained on the breast cell nuclei, yielding high accuracy on reserved breast nuclei images (AUC 97-99%) However, the breast cell-trained deep learning model yielded poor classifications on the colorectal nuclei (AUC 56%), a much worse cross-classification than tile-based WSI-level analysis of TCGA data (FIG. 7A). Additionally, the effects of summing across nuclei within the colorectal ROIs (thousands of cells each) was tested to see if such summation would improve purity predictions. However, even aggregated over full ROIs the nucleus-based RMSE was 25%, an RMSE higher than the tile-based analysis of the same data (20%). This suggests that, although the tile-based approach is not aware of individual cells, it compensates by using intercellular regions of images.

To perform tile-based purity estimation, Inception, DenseNet, and Xception-based transfer learning models were used and each trained for 20 epochs, where the network at the epoch >10 performing best on test data and having test mean squared error larger than the train set is used for validation. Tiles of size 128×128 resulted in large test errors, and the ROIs were too small for 1024×1024 tiles. Tiles of sizes 512 and 256, and tiles of size 512 were focused on for validation. For cases with reduced magnification 512-by-512 tiles were down-sampled by a factor of two. To correct for acquisition differences between breast and colon cancer ROIs, the tile histogram distribution was equalized. For each tile, purity was defined as the ratio of tumor cells to total cells, with a slight adjustment to avoid purities too close to zero or one, as these may destabilize the analysis. For example, for a tile with purity value p, log it purity was computed as $\log((p+0.05)/(1.05-p))$. The log it purity was then inverted to obtain adjusted TPF values. Overlapping tiles were used with step size 64 pixels for both tile sizes. Given the extracted features, a fully-connected layer of 256 neurons with ReLU non-linearity, followed by a drop out of 25%, and a fully connected neuron using the sigmoid activation was used to perform classification. The "he_normal" initialization method of Keras was used, and an elastic net regularization setting L1 and L2 penalties to 0.0001.

To perform nucleus-based purity estimation, the network of Hlavcheva et al. (2019) was implemented including their reported hyperparameters. The goal of this method is to classify individual nuclei as either cancerous or non-cancerous. Nucleus patches were resized to 32 by 32 pixels. To adjust for acquisition differences between the breast and colon datasets histogram equalization was applied to both datasets. The network was trained on the BreCaHAD training set and tested on the reserved breast data across all individual nuclei, finding high accuracy (AUC 97-99%). For comparison, a transfer-learning approach was also tested. The transfer learning pipeline used similar image preprocessing, except the nucleus patches were resized to 128 by 128 pixels because Inception requires images to be larger than 75 by 75 pixels. The fully-trained method was superior to transfer-learning (all transfer learning AUCs<65%, over various parameter choices). Therefore for analysis of the colon cancer dataset, the Hlavcheva fully-trained method was used, trained on the entire BreCaHAD dataset. For predictions of TPF on ROIs, the sum of predicted tumor probabilities was compared across all nuclei to the pathologist purity annotations of all cells in the ROI.

VI. Computer Implementation

Figure 17:
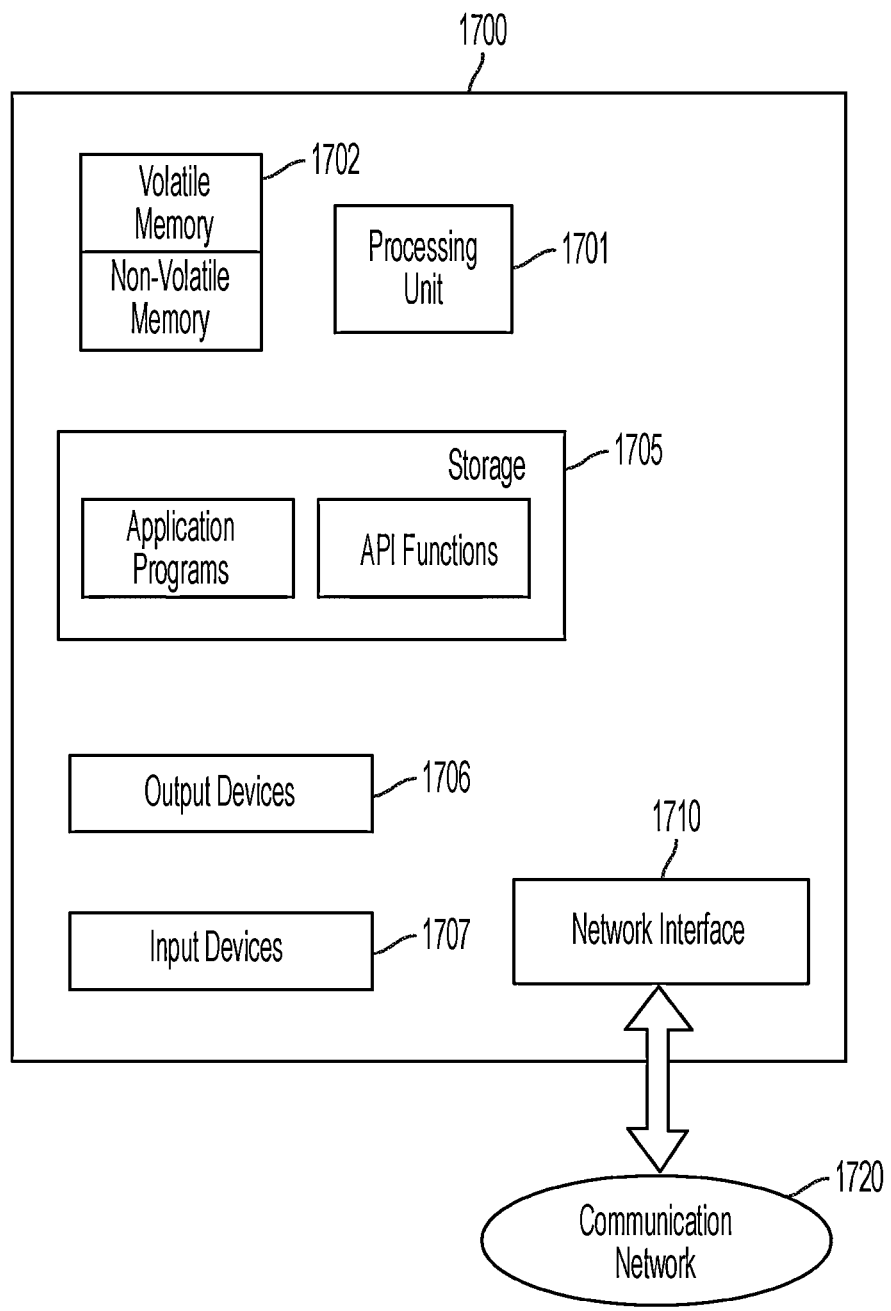
FIG. 17 depicts, schematically, an illustrative computing device 1700 on which any aspect of the present disclosure may be implemented.

FIG. 17 shows, schematically, an illustrative computer 1700 on which any aspect of the present disclosure may be implemented. The computer 1700 includes a processing unit 1701 having one or more processors and a non-transitory computer-readable storage medium 1702 that may include, for example, volatile and/or non-volatile memory. The memory 1702 may store one or more instructions to program the processing unit 1701 to perform any of the functions described herein. The computer 1700 may also include other types of non-transitory computer-readable medium, such as storage 1705 (e.g., one or more disk drives) in addition to the system memory 1702. The storage 1705 may also store one or more application programs and/or resources used by application programs (e.g., software libraries), which may be loaded into the memory 1702.

The computer 1700 may have one or more input devices and/or output devices, such as devices 1706 and 1707 illustrated in FIG. 17. These devices may be used, for instance, to present a user interface. Examples of output devices that may be used to provide a user interface include printers and display screens for visual presentation of output, and speakers and other sound generating devices for audible presentation of output. Examples of input devices that may be used for a user interface include keyboards and pointing devices (e.g., mice, touch pads, and digitizing tablets). As another example, the input devices 1707 may include a microphone for capturing audio signals, and the output devices 1706 may include a display screen for visually rendering, and/or a speaker for audibly rendering, recognized text.

In the example shown in FIG. 17, the computer 1700 also includes one or more network interfaces (e.g., the network interface 1710) to enable communication via various networks (e.g., the network 1720). Examples of networks include a local area network (e.g., an enterprise network) and a wide area network (e.g., the Internet). Such networks may be based on any suitable technology and operate according to any suitable protocol, and may include wireless networks and/or wired networks (e.g., fiber optic networks).

Having thus described several aspects of at least one embodiment, it is to be appreciated that various alterations, modifications, and improvements will readily occur to those skilled in the art.

Such alterations, modifications, and improvements are intended to be part of this disclosure, and are intended to be within the spirit and scope of the described technology. Further, though advantages of the present embodiments are indicated, it should be appreciated that not every embodiment of the technology described herein will include every described advantage. Some embodiments may not implement any features described as advantageous herein and in some instances one or more of the described features may be implemented to achieve further embodiments. Accordingly, the foregoing description and drawings are by way of example only.

The above-described embodiments of the technology described herein can be implemented in any of numerous ways. For example, the embodiments may be implemented using hardware, software or a combination thereof. When implemented in software, the software code can be executed on any suitable processor or collection of processors, whether provided in a single computer or distributed among multiple computers. Such processors may be implemented as integrated circuits, with one or more processors in an integrated circuit component, including commercially available integrated circuit components known in the art by names such as CPU chips, GPU chips, microprocessor, microcontroller, or co-processor. Alternatively, a processor may be implemented in custom circuitry, such as an ASIC, or semi-custom circuitry resulting from configuring a programmable logic device. As yet a further alternative, a processor may be a portion of a larger circuit or semiconductor device, whether commercially available, semi-custom or custom. As a specific example, some commercially available microprocessors have multiple cores such that one or a subset of those cores may constitute a processor. Though, a processor may be implemented using circuitry in any suitable format.

Also, the various methods or processes outlined herein may be coded as software that is executable on one or more processors running any one of a variety of operating systems or platforms. Such software may be written using any of a number of suitable programming languages and/or programming tools, including scripting languages and/or scripting tools. In some instances, such software may be compiled as executable machine language code or intermediate code that is executed on a framework or virtual machine. Additionally, or alternatively, such software may be interpreted.

The techniques disclosed herein may be embodied as a non-transitory computer-readable medium (or multiple computer-readable media) (e.g., a computer memory, one or more floppy discs, compact discs, optical discs, magnetic tapes, flash memories, circuit configurations in Field Programmable Gate Arrays or other semiconductor devices, or other non-transitory, tangible computer storage medium) encoded with one or more programs that, when executed on one or more processors, perform methods that implement the various embodiments of the present disclosure discussed above. The computer-readable medium or media may be transportable, such that the program or programs stored thereon may be loaded onto one or more different computers or other processors to implement various aspects of the present disclosure as discussed above.

The terms "program" or "software" are used herein to refer to any type of computer code or set of computer-executable instructions that may be employed to program one or more processors to implement various aspects of the present disclosure as discussed above. Moreover, it should be appreciated that according to one aspect of this embodiment, one or more computer programs that, when executed, perform methods of the present disclosure need not reside on a single computer or processor, but may be distributed in a modular fashion amongst a number of different computers or processors to implement various aspects of the present disclosure.

Computer-executable instructions may be in many forms, such as program modules, executed by one or more computers or other devices. Program modules may include routines, programs, objects, components, data structures, etc. that perform particular tasks or implement particular abstract data types. Functionalities of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields to locations in a computer-readable medium that convey relationship between the fields. However, any suitable mechanism may be used to establish a relationship between information in fields of a data structure, including through the use of pointers, tags, or other mechanisms that establish relationship between data elements.

Various aspects of the present technology may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the technology may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

The described technology may be embodied in the following configurations:

(1) A system for identifying cancerous tissue in a tissue sample, the system comprising: at least one processor operatively connected to a memory containing instructions which, when executed by the at least one processor, cause the at least one processor to: instantiate a container-based processing architecture comprising: a first container configured to process at least one whole slide image (WSI) of the tissue sample to obtain an at least one processed WSI; a second container configured to provide the at least one processed WSI as input to a trained deep learning model to obtain feature values output by the trained deep learning model; and a third container configured to classify the at least one WSI as one of an image comprising non-cancerous tissue or an image comprising cancerous tissue based on the feature values.

(2) The system of (1), wherein one or more layers of the trained deep learning model are trained based on a training set of images comprising a plurality of WSIs of tissue.

(3) The system of any one of (1)-(2), wherein all of the layers of the trained deep learning model are trained based on the training set of images comprising a plurality of WSIs of tissue.

(4) The system of any one of (1)-(3), wherein the plurality of WSIs comprise WSIs of a plurality of tissue types.

(5) The system of any one of (1)-(4), wherein the plurality of tissue types include at least one of a selection of sarcoma tissue, brain tissue, breast tissue, cervical tissue, esophageal tissue, lung tissue, kidney tissue, stomach tissue, uterine tissue, and/or testicular tissue.

(6) The system of any one of (1)-(5), wherein one or more layers of the trained deep learning model are trained based on a training set of images comprising non-histological images.

(7) The system of any one of (1)-(6), wherein the trained deep learning model is trained using a plurality of WSIs, the plurality of WSIs comprising WSIs of tissues that are a different tissue type that a tissue type of the tissue sample.

(8) The system of any one of (1)-(7), wherein the first container is configured to process the at least one WSI by sectioning the at least one WSI into a plurality of tiles.

(9) The system of any one of (1)-(8), wherein tiles of the plurality of tiles are non-overlapping within the at least one WSI.

(10) The system of any one of (1)-(9), wherein the first container is configured to process the at least one WSI by removing one or more background pixels from the at least one WSI.

(11) The system of any one of (1)-(10), wherein the trained deep learning model is a convolutional neural network.

(12) The system of any one of (1)-(11), wherein the trained deep learning model comprises an Inception v3 network.

(13) The system of any one of (1)-(12), wherein the trained deep learning model comprises a fully connected layer connected to an output of the Inception v3 network.

(14) The system of any one of (1)-(13), wherein the fully connected layer is trained based on the training set of images comprising the plurality of WSIs of tissue.

(15) The system of any one of (1)-(14), wherein the fully connected layer comprises 1024 neurons.

(16) The system of any one of (1)-(15), further comprising a fourth container configured to identify, based on the feature values, a cancer subtype of the tissue sample.

(17) The system of any one of (1)-(16), wherein the cancer subtype comprises at least one of brain subtypes: oligoastrocytoma, oligodendroglioma, and/or astrocytoma; breast subtypes: mucinous, mixed, lobular, and/or ductal; cervical subtypes: adenoma and/or squamous cell carcinoma; esophageal subtypes: adenocarcinoma and/or squamous cell carcinoma; kidney subtypes: chromophobe, clear cell, and/or papillary; lung subtypes: adenocarcinoma and/or squamous cell carcinoma; sarcoma subtypes: myxofibrosarcoma, undifferentiated pleomorphic sarcoma, dedifferentiated liposarcoma, and/or leiomyosarcomas; stomach subtypes: diffuse and/or intestinal; testicular subtypes: non-seminoma and/or seminoma; thyroid subtypes: tall, follicular, and/or classical; and/or uterine subtypes: carcinoma and/or carcinosarcoma.

(18) At least one non-transitory computer readable storage medium storing processor-executable instructions that, when executed by at least one processor, cause the at least one processor to perform a method comprising: processing at least one whole slide image (WSI) of a tissue sample; and classifying, using a trained deep learning model, the at least one WSI as comprising one of an image comprising cancerous tissue or an image comprising non-cancerous tissue, wherein: at least one layer of the trained deep learning model is trained based on a first training data set comprising WSIs of a plurality of tissue types, and at least one layer of the trained deep learning model is trained based on a second training data set comprising non-histological images.

(19) The at least one non-transitory computer readable storage medium of (18), wherein the first training data set comprises WSIs of a plurality of tissue types that are different from a tissue type of the tissue sample.

(20) The at least one non-transitory computer readable storage medium of any one of (18)-(19), wherein the plurality of tissue types include at least one of a selection of sarcoma tissue, brain tissue, breast tissue, cervical tissue, esophageal tissue, lung tissue, kidney tissue, stomach tissue, uterine tissue, and/or testicular tissue.

(21) The at least one non-transitory computer readable storage medium of any one of (18)-(20), wherein processing the at least one WSI comprises sectioning the at least one WSI into a plurality of tiles.

(22) The at least one non-transitory computer readable storage medium of any one of (18)-(21), wherein sectioning the at least one WSI into a plurality of tiles comprises sectioning the at least one WSI into a plurality of non-overlapping tiles.

(23) The at least one non-transitory computer readable storage medium of any one of (18)-(22), wherein processing the at least one WSI comprises removing one or more background pixels from the at least one WSI.

(24) The at least one non-transitory computer readable storage medium of any one of (18)-(23), wherein classifying the at least one WSI using the trained deep learning model comprises using a convolutional neural network.

(25) The at least one non-transitory computer readable storage medium of any one of (18)-(24), wherein using the convolutional neural network comprises using an Inception v3 network.

(26) The at least one non-transitory computer readable storage medium of any one of (18)-(25), wherein using the convolutional neural network comprises using a fully connected layer connected to an output of the Inception v3 network.

(27) The at least one non-transitory computer readable storage medium of any one of (18)-(26), further comprising identifying, based on feature values output by the trained deep learning model, a cancer subtype of the tissue sample.

(28) The at least one non-transitory computer readable storage medium of any one of (18)-(27), wherein identifying the cancer subtype of the tissue sample comprises identifying the cancer subtype as belonging to one of a group of: brain subtypes: oligoastrocytoma, oligodendroglioma, and/or astrocytoma; breast subtypes: mucinous, mixed, lobular, and/or ductal; cervical subtypes: adenoma and/or squamous cell carcinoma; esophageal subtypes: adenocarcinoma and/or squamous cell carcinoma; kidney subtypes: chromophobe, clear cell, and/or papillary; lung subtypes: adenocarcinoma and/or squamous cell carcinoma; sarcoma subtypes: myxofibrosarcoma, undifferentiated pleomorphic sarcoma, dedifferentiated liposarcoma, and/or leiomyosarcomas; stomach subtypes: diffuse and/or intestinal; testicular subtypes: non-seminoma and/or seminoma; thyroid subtypes: tall, follicular, and/or classical; and/or uterine subtypes: carcinoma and/or carcinosarcoma.

(29) A method for identifying cancerous tissue in a whole slide image (WSI) of a tissue sample, the method comprising: processing at least one WSI of the tissue sample; and classifying, using a trained deep learning model, the at least one WSI as comprising one of an image comprising cancerous tissue or an image comprising non-cancerous tissue, wherein: at least one layer of the trained deep learning model is trained based on a first training data set comprising WSIs of a plurality of tissue types, and at least one layer of the trained deep learning model is trained based on a second training data set comprising non-histological images.

(30) A method for identifying a genetic mutation of a cancerous tissue sample based on a whole slide image (WSI) of the cancerous tissue sample, the method comprising: processing at least one WSI of the cancerous tissue sample; and classifying, using a trained deep learning model, the at least one WSI as an image comprising one of cancerous tissue having a genetic mutation or one of cancerous tissue lacking a genetic mutation.

(31) The method of (30), wherein the genetic mutation is a TP53 mutation.

(32) The method of any one of (30)-(31), wherein the cancerous tissue sample may be a sample of one of breast, lung and/or gastric tissue.

(33) The method of any one of (30)-(32), wherein the trained deep learning model is trained based on a training set of images comprising a plurality of WSIs of tissue.

(34) The method of any one of (30)-(33), wherein the plurality of WSIs comprise WSIs of a plurality of tissue types.

(35) The method of any one of (30)-(34), wherein the plurality of tissue types include at least one of a selection of sarcoma tissue, brain tissue, breast tissue, cervical tissue, esophageal tissue, lung tissue, kidney tissue, stomach tissue, uterine tissue, and/or testicular tissue.

(36) The method of any one of (30)-(35), wherein processing the at least one WSI comprises sectioning the at least one WSI into a plurality of tiles.

(37) The method of any one of (30)-(36), wherein sectioning the at least one WSI into a plurality of tiles comprises sectioning the at least one WSI into a plurality of non-overlapping tiles.

(38) The method of any one of (30)-(37), wherein processing the at least one WSI comprises removing one or more background pixels from the at least one WSI.

(39) The method of any one of (30)-(38), wherein classifying the at least one WSI using the trained deep learning model comprises using a convolutional neural network.

(40) The method of any one of (30)-(39), wherein using the convolutional neural network comprises using an Inception v3 network.

(41) The method of any one of (30)-(40), wherein using the convolutional neural network comprises using a fully connected layer connected to an output of the Inception v3 network.

(42) The method of any one of (30)-(41), further comprising: selecting a treatment modality based on the classification of the at least one WSI; and administering the selected treatment modality to the patient.

(43) The method of any one of (30)-(42), wherein classifying the at least one WSI as comprising one of an image of cancerous tissue having a genetic mutation comprises classifying the at least one WSI as comprising one of an image of cancerous tissue having a HER2-positive genetic mutation.

(44) The method of any one of (30)-(43), wherein: selecting a treatment modality based on the classification comprises selecting a treatment modality including trastuzumab; and administering the selected treatment modality to the patient includes administering trastuzumab to the patient.

(45) At least one non-transitory computer readable storage medium storing processor-executable instructions that, when executed by at least one processor, cause the at least one processor to perform a method comprising: processing at least one WSI of a cancerous tissue sample; and classifying, using a trained deep learning model, the at least one WSI as comprising one of an image of cancerous tissue having a genetic mutation or one of an image comprising cancerous tissue lacking a genetic mutation.

(46) A system for identifying a genetic mutation of a cancerous tissue sample, the system comprising: at least one processor operatively connected to a memory containing instructions which, when executed by the at least one processor, cause the at least one processor to: instantiate a container-based processing architecture comprising: a first container configured to process at least one whole slide image (WSI) of the cancerous tissue sample to obtain an at least one processed WSI; a second container configured to provide the at least one processed WSI as input to a trained deep learning model to obtain feature values output by the trained deep learning model; and a third container configured to classify the at least one WSI as one of an image of cancerous tissue having a genetic mutation or one of an image comprising cancerous tissue lacking a genetic mutation based on the feature values.

(47) The system of (46), wherein the genetic mutation is a TP53 mutation.

(48) The system of any one of (46)-(47), wherein the cancerous tissue sample may be a sample of one of breast, lung and/or gastric tissue.

(49) The system of any one of (46)-(48), wherein the trained deep learning model is trained based on a training set of images comprising a plurality of WSIs of tissue.

(50) The system of any one of (46)-(49), wherein the plurality of WSIs comprise WSIs of a plurality of tissue types.

(51) The system of any one of (46)-(50), wherein the plurality of tissue types include at least one of a selection of sarcoma tissue, brain tissue, breast tissue, cervical tissue, esophageal tissue, lung tissue, kidney tissue, stomach tissue, uterine tissue, and/or testicular tissue.

(52) The system of any one of (46)-(51), wherein the first container is configured to process the at least one WSI by sectioning the at least one WSI into a plurality of tiles.

(53) The system of any one of (46)-(52), wherein tiles of the plurality of tiles are non-overlapping within the at least one WSI.

(54) The system of any one of (46)-(53), wherein the first container is configured to process the at least one WSI by removing one or more background pixels from the at least one WSI.

(55) The system of any one of (46)-(54), wherein the trained deep learning model is a convolutional neural network.

(56) The system of any one of (46)-(55), wherein the convolutional neural network comprises an Inception v3 network.

(57) The system of any one of (46)-(56), wherein the convolutional neural network comprises using a fully connected layer connected to an output of the Inception v3 network.

What is claimed is:

1. A method for identifying a genetic mutation of a cancerous tissue sample based on a whole slide image (WSI) of the cancerous tissue sample, the method comprising:
   processing the WSI of the cancerous tissue sample; and
   classifying, using a trained deep learning model, the WSI as an image comprising one of cancerous tissue having a genetic mutation or one of cancerous tissue lacking a genetic mutation, wherein:
   the trained deep learning model is trained based on a training set of images comprising a plurality of WSIs of a plurality of tissue types obtained from a plurality of different organs.

2. The method of claim 1, wherein the genetic mutation is a TP53 mutation.

3. The method of claim 1, wherein the cancerous tissue sample may be a sample of one of breast, lung and/or gastric tissue.

4. The method of claim 1, wherein the plurality of tissue types include at least one of a selection of sarcoma tissue, brain tissue, breast tissue, cervical tissue, esophageal tissue, lung tissue, kidney tissue, stomach tissue, uterine tissue, and/or testicular tissue.

5. The method of claim 1, wherein processing the WSI comprises sectioning the WSI into a plurality of tiles.

6. The method of claim 5, wherein sectioning the WSI into a plurality of tiles comprises sectioning the WSI into a plurality of non-overlapping tiles.

7. The method of claim 1, wherein processing the WSI comprises removing one or more background pixels from the WSI.

8. The method of claim 1, wherein classifying the WSI using the trained deep learning model comprises using a convolutional neural network.

9. The method of claim 8, wherein using the convolutional neural network comprises using an Inception v3 network.

10. The method of claim 9, wherein using the convolutional neural network comprises using a fully connected layer connected to an output of the Inception v3 network.

11. The method of claim 1, further comprising:
   selecting a treatment modality based on the classification of the WSI; and
   administering the selected treatment modality to a patient.

12. The method of claim 11, wherein:
   selecting a treatment modality based on the classification comprises selecting a treatment modality including trastuzumab; and
   administering the selected treatment modality to the patient includes administering trastuzumab to the patient.

13. The method of claim 1, wherein classifying the WSI as comprising one of an image of cancerous tissue having a genetic mutation comprises classifying the WSI as comprising one of an image of cancerous tissue having a HER2-positive genetic mutation.

14. At least one non-transitory computer readable storage medium storing processor-executable instructions that, when executed by at least one processor, cause the at least one processor to perform a method comprising:
   processing a whole slide image (WSI) of a cancerous tissue sample; and
   classifying, using a trained deep learning model, the WSI as comprising one of an image of cancerous tissue having a genetic mutation or one of an image comprising cancerous tissue lacking a genetic mutation, wherein:
   the trained deep learning model is trained based on a training set of images comprising a plurality of WSIs of a plurality of tissue types obtained from a plurality of different organs.

15. The at least one non-transitory computer readable storage medium of claim 14, wherein processing the WSI comprises:
   sectioning the WSI into a plurality of non-overlapping tiles; and
   removing one or more background pixels from the WSI.

* * * * *